United States Patent [19]

Doll et al.

[11] Patent Number: 5,712,280

[45] Date of Patent: Jan. 27, 1998

[54] TRICYCLIC COMPOUNDS USEFUL FOR INHIBITION OF G-PROTEIN FUNCTION AND FOR TREATMENT OF PROLIFERATIVE DISEASES

[75] Inventors: Ronald J. Doll, Maplewood; Alan K. Mallams, Hackettstown; Adriano Afonso, West Caldwell; Dinanath F. Rane, Morganville; Randall R. Rossman, Nutley; F. George Njoroge, Union, all of N.J.

[73] Assignee: Schering Corporation, Kenilworth, N.J.

[21] Appl. No.: 418,973

[22] Filed: Apr. 7, 1995

[51] Int. Cl.$^6$ .................. A61K 31/495; C07D 401/06
[52] U.S. Cl. .................. 514/253; 514/255; 514/227.8; 514/228.2; 514/232.8; 514/235.5; 544/60; 544/121; 544/360; 544/361; 544/380
[58] Field of Search .................. 514/255, 253, 514/227.8, 228.2, 232.8, 235.5; 544/60, 121, 360, 361, 380

[56] References Cited

U.S. PATENT DOCUMENTS

| 4,282,233 | 8/1981 | Villani | 424/260 |
|---|---|---|---|
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |

FOREIGN PATENT DOCUMENTS

| 0042544 | 12/1981 | European Pat. Off. |
|---|---|---|
| 0270818 | 6/1988 | European Pat. Off. |
| 0396083 | 11/1990 | European Pat. Off. |
| 0495484 | 7/1992 | European Pat. Off. |
| 0535730 | 4/1993 | European Pat. Off. |
| WO88/03138 | 5/1988 | WIPO |
| WO89/10363 | 11/1989 | WIPO |
| WO90/13548 | 11/1990 | WIPO |
| WO92/00293 | 1/1992 | WIPO |
| WO92/11034 | 7/1992 | WIPO |
| WO94/04561 | 3/1994 | WIPO |
| WO94/24107 | 10/1994 | WIPO |
| WO95/00497 | 1/1995 | WIPO |

OTHER PUBLICATIONS

Cell, 65, 1–4 (1991).
J. Biol. Chem., 266, (24) 15575–15578 (1991).
Proc. Natl. Acad. Sci. USA, 87, 3042–3046 (1990).
Proc. Natl. Acad. Sci. USA, 88, 8631–8635 (1991).
Nature, 356, 713–715 (1992).
Proc. Natl. Acad. Sci. USA, 87, 7541–7545 (1990).
J. Biol. Chem., 265, (25) 14701–14704 (1990).
Proc. Natl. Acad. Sci. USA, 87, 7926–7929 (1990).
Cell, 62, 81–88 (1990).
Biochemistry, 31, 3800–3807, (1990).
Science, 260 (1993), 1934–1937.
Science, 260 (1993), 1937–1942.
Piwinski, et al., J. Med. Chem., 34, (1) 457–461 (1991).
Chem. Abstracts No. 121:53129x (1994) for WO94/04561.
Sebti, et al., Proc. Ann. Meeting AM Assoc. Cancer Res., 33:A2217 (1992).
Villani, et al., J. Med. Chem., 15, (7) 750–754 (1972).
Billah, et al., Lipids, 26, (12) 1172–1174 (1991).
Villani, et al., Arzneim.-Forsch./Drug Res., 36(II), 1311–1314 (1986).

Primary Examiner—Joseph McKane
Attorney, Agent, or Firm—Henry C. Jeanette

[57] ABSTRACT

Novel compounds of Formula

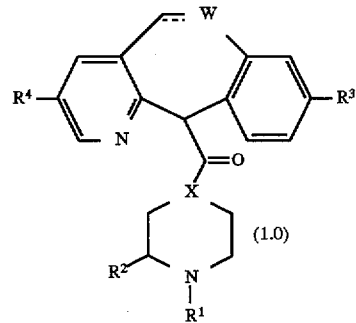

are disclosed.

Also disclosed is a method of inhibiting Ras function and therefore inhibiting the abnormal growth of cells. The method comprises administering a compound of the Formula 1.0 to a biological system. In particular, the method inhibits the abnormal growth of cells in a mammal such as a human being.

20 Claims, No Drawings

TRICYCLIC COMPOUNDS USEFUL FOR INHIBITION OF G-PROTEIN FUNCTION AND FOR TREATMENT OF PROLIFERATIVE DISEASES

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

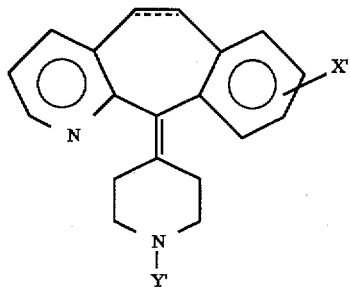

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, $SO_2R'$ wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed calls. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro: (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

The compounds useful in the claimed methods are novel compounds represented by Formula 1.0:

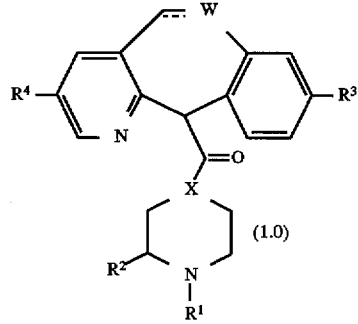

or a pharmaceutically acceptable salt or solvate thereof, wherein:

(1) $R^1$ is a group selected from:

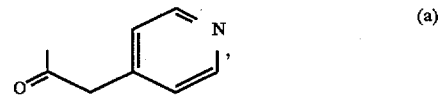
(a)

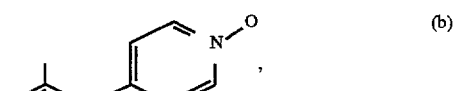
(b)

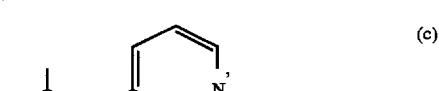
(c)

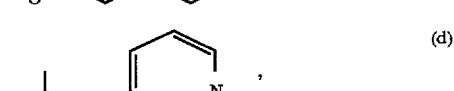
(d)

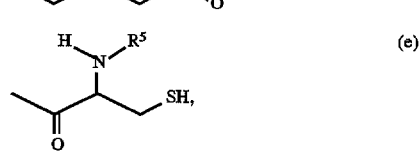
(e)

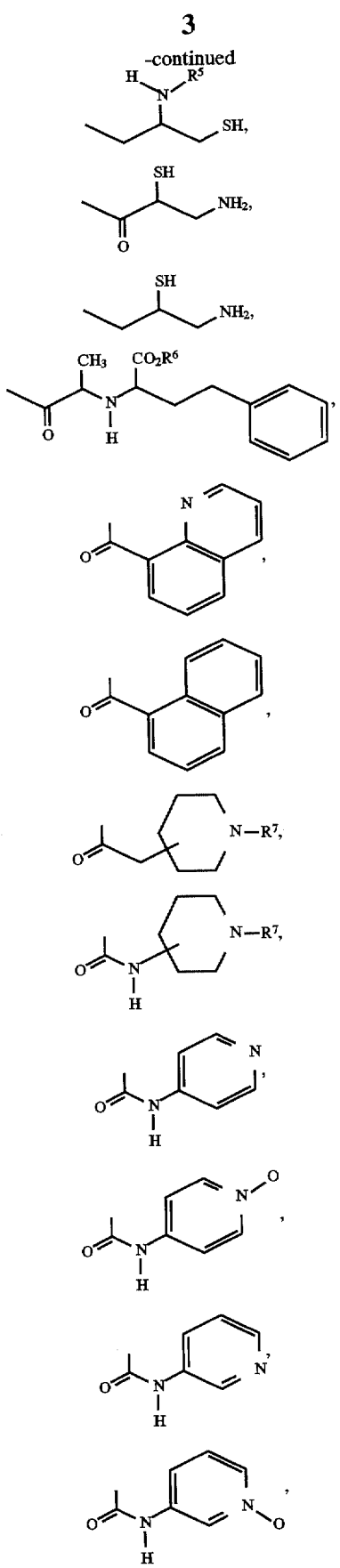
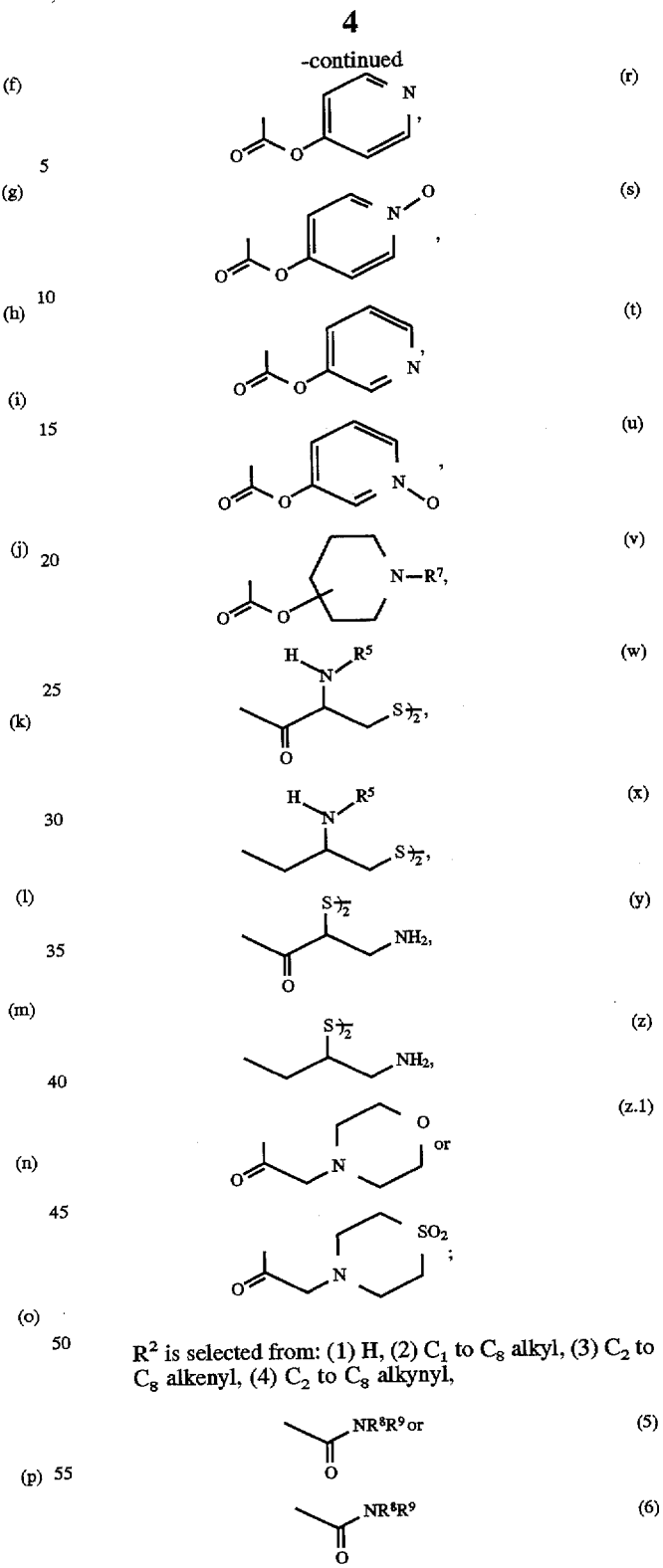

$R^2$ is selected from: (1) H, (2) $C_1$ to $C_8$ alkyl, (3) $C_2$ to $C_8$ alkenyl, (4) $C_2$ to $C_8$ alkynyl, (5) —C(O)—$NR^8R^9$ or (6) —C(O)—$NR^8R^9$ wherein said alkyl, alkenyl, or alkynyl is optionally substituted with one or more groups independently selected from:
(a) aryl, aralkyl, heteroaryl, heteroarylalkyl or heterocycloalkyl; said aryl, aralkyl, heteroaryl, heteroarylalkyl or heterocycloalkyl optionally substituted with one or more groups independently selected from:
(1) $C_1$ to $C_4$ alkyl,
(2) $(CH_2)_t OR^8$ wherein t is 1 to 4, (3) $(CH_2)_tNR^8R^9$ wherein t is 1 to 4, or
(4) halogen,
(b) $C_3$ to $C_6$ cycloalkyl,
(c) $-OR^8$,
(d) $-SR^8$,
(e) $-S(O)R^8$,
(f) $-SO_2R^8$,
(g) $-NR^8R^9$,
(h)

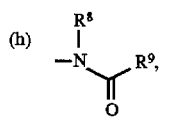

(i)
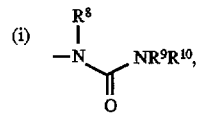

(j)
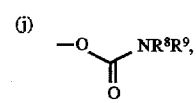

(k)
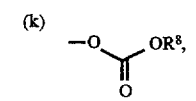

(l)
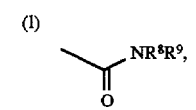

(m) $-SO_2-NR^8R^9$, (n)

(o)
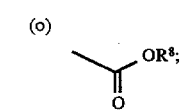

$R^3$ is selected from H, halogen or $C_1$ to $C_6$ alkyl (e.g., methyl);

$R^4$ is selected from H, halogen or $C_1$ to $C_6$ alkyl (e.g., methyl);

$R^5$ is selected from: H,

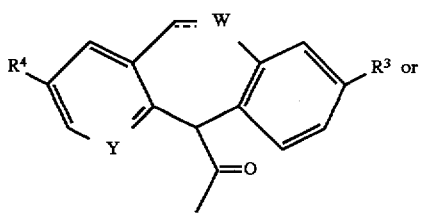 or

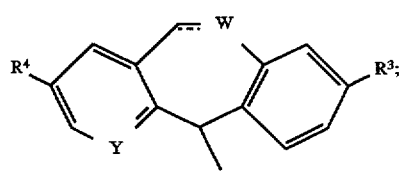
(bb)

$R^6$ is selected from H or $C_1$ to $C_6$ alkyl (preferably methyl or ethyl);

$R^7$ is selected from H, $C_1$ to $C_6$ alkyl, haloalkyl, or $-C(O)R^{11}$ wherein $R^{11}$ is selected from $C_1$ to $C_6$ alkyl, $C_1$ to $C_6$ alkoxy or $-NHR^{12}$ (wherein $R^{12}$ is $C_1$ to $C_6$ alkyl or H), or $R^7$ is an acyl radical of a naturally occurring amino acid;

$R^8$, $R^9$ and $R^{10}$ am independently selected from H, $C_1$ to $C_4$ alkyl, $C_3$ to $C_6$ cycloalkyl, heteroaryl, heteroarylalkyl, heterocycloalkyl, aryl or aralkyl; said alkyl, cycloalkyl, heteroaryl, heteroarylalkyl, heterocycloalkyl, aryl or aralkyl are optionally substituted with $C_1$ to $C_4$ alkoxy, aryl, heteroaryl, heterocycloalkyl, cyclopropyl, halogen, $-OH$, $-C(O)R^{13}$, $-SO_2R^{13}$, or $-NR^{14}R^{15}$ wherein $R^{13}$ is selected from $C_1$ to $C_4$ alkyl or aralkyl, and wherein $R^{14}$ and $R^{15}$ are independently selected from H, $C_1$ to $C_4$ alkyl or aralkyl; with the proviso that $R^8$ is not H in substituents (e), (f) or (k), and with the proviso that $R^9$ is not H in substituent (h) or (n), and with the proviso that $R^8$, $R^9$, or $R^{10}$ is not $-CH_2OH$ or $-CH_2NR^{14}R^{15}$ when $R^8$, $R^9$, or $R^{10}$ is directly attached to a heteroatom (e.g., O, S or N).

optionally, when $R^8$ and $R^9$ are bound to the same nitrogen, $R^8$ and $R^9$, together with the nitrogen to which they are bound, form a 5 to 7 membered heterocycloalkyl ring;

optionally, when $R^9$ and $R^{10}$ are bound to the same nitrogen, $R^9$ and $R^{10}$, together with the nitrogen to which they are bound, form a 5 to 7 membered heterocycloalkyl ring;

—represents an optional bond;

W is selected from CH when the optional bond is present, or O, S or $CH_2$ when the optional bond is absent;

X is selected from CH or N; and

Y is selected from N or CH.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

Ac—represents acetyl;

acyl radical of a naturally occurring amino acid—means a group of the formula —C(O)C(NH$_2$)R$^{26}$R$^{28}$, i.e.:

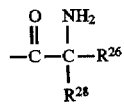

wherein R$^{26}$ and R$^{28}$ represent the substituents of the amino acid bound to the α-carbon; for example R$^{26}$ and R$^{28}$ can be independently selected from H, alkyl, or alkyl substituted with an R$^{30}$ group, wherein R$^{30}$ can be, for example, —OH, SH, —SCH$_3$, —NH$_2$, phenyl, p-hydroxyphenyl, indolyl or imidazolyl, such that HO—C(O)C(NH$_2$)R$^{26}$R$^{28}$ is an amino acid selected from, for example, alanine, cysteine, cystine, glycine, histidine, isoleucine, leucine, lysine, methionine, phenylalanine, serine, tryptophane, tyrosine or valine;

alkyl—(including the alkyl portions of alkoxy, alkylamino and dialkylamino)—represents straight and branched carbon chains and contains from one to twenty carbon atoms, preferably one to six carbon atoms;

alkenyl—represents straight and branched carbon chains having at least one carbon to carbon double bond and containing from 2 to 12 carbon atoms, preferably from 2 to 6 carbon atoms and most preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aralkyl—represents an alkyl group, as defined above, wherein one or more hydrogen atoms have been replaced by aryl groups, as defined below (e.g., benzyl);

aryl (including the aryl portion of aryloxy and aralkyl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, amino, alkylamino, dialkylamino, —COOR$^{16}$ (wherein R$^{16}$ represents H, alkyl, aryl or aralkyl (e.g., benzyl)), or —NO$_2$; and Bu—represents butyl;

cycloalkyl—represents saturated carbocyclic rings branched or unbranched of from 3 to 20 carbon atoms, preferably 3 to 7 carbon atoms;

Et—represents ethyl;

halogen (halo)—represents fluoro, chloro, bromo and iodo;

haloalkyl—represents an alkyl group, as defined above, wherein one or more hydrogen atoms have been replaced by halogen atoms;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —N— (suitable heterocycloalkyl groups include 2- or 3-tetrahydrofuranyl, 2- or 3- tetrahydrothienyl, 2-, 3- or 4-piperidinyl, 2- or 3-pyrrolidinyl, 2- or 3-piperizinyl, 2- or 4-dioxanyl, etc.);

heteroaryl—represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with R$^3$ and R$^4$), wherein pyridyl N-oxide can be represented as:

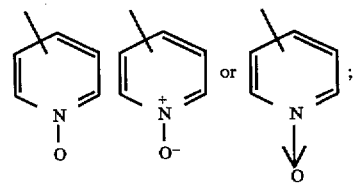

heteroarylalkyl—represents an alkyl group (as defined above) wherein one or more hydrogen atoms have been replaced by heteroaryl groups (as defined above); and Ph—represents phenyl.

Representative compounds of the present invention include:

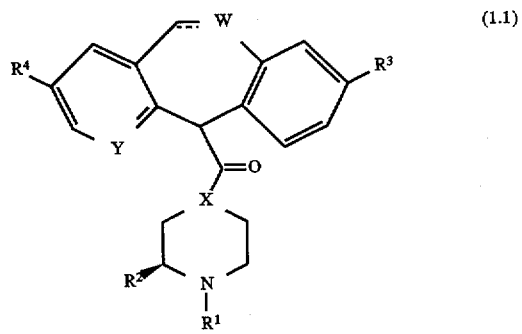

(1.1)

For the compounds of this invention, W is preferably CH or CH$_2$, with CH$_2$ being most preferred; Y is preferably N; X is preferably N; R$^3$ is preferably halogen, with Br, Cl or I being most preferred, and Cl being even more preferred;

and $R^4$ is preferably halogen, with Br, Cl or I being most preferred, and Br being even more preferred.

Representative compounds of this invention include those wherein $R^1$ is selected from:

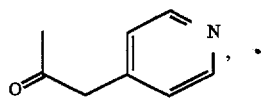 (a)

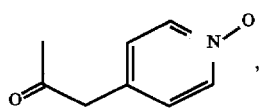 (b)

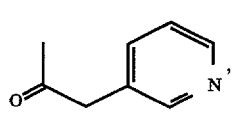 (c)

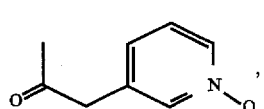 (d)

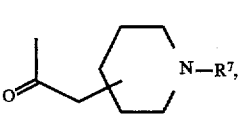 (l)

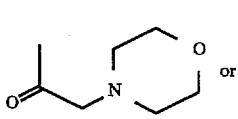 or (z.1)

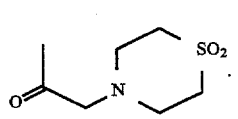 (z.2)

Representative compounds of this invention also include those wherein $R^1$ is selected from:

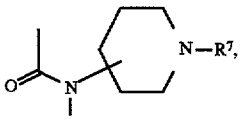 (m)

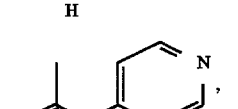 (n)

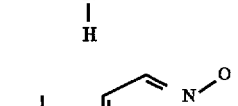 (o)

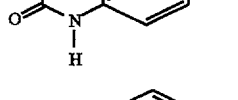 or (p)

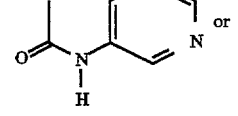 (q)

Representative compounds of this invention include compounds wherein $R^1$ is selected from:

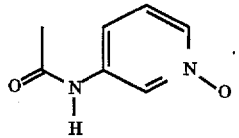 (r)

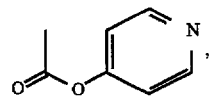 (s)

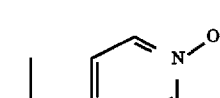 (t)

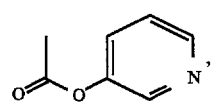 or (u)

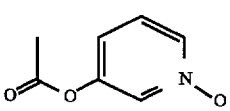 (v)

Representative compounds of this invention further include compounds wherein $R^1$ is selected from:

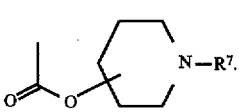 (e)

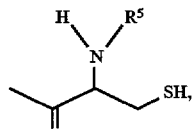 (f)

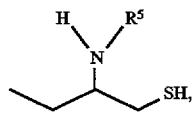 or (g)

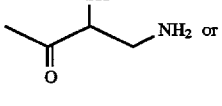 (h)

Representative compounds of this invention also include compounds wherein $R^1$ is selected from:

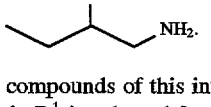 (w)

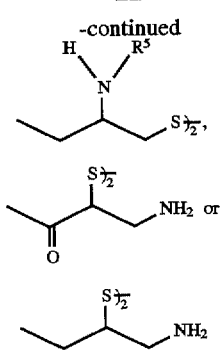

Generally R¹ is

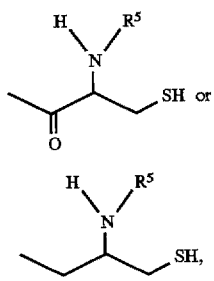

and usually R¹ is represented by Formula (e) or (f) above wherein R⁵ is hydrogen.

Those skilled in the art will appreciate that R¹ substituents (e), (f), (g) and (h) can exist as the disulfide substituents (w), (x), (y) and (z), respectively.

Preferably, R² is selected from H, —C₄H₉, —CH₂C₆H₅, —CH₂CH₂OCH₃, —CH₂CH₂SCH₃, —CH₂CH₂O-n-C₃H₇, —CH₂CH₂CH₂OCH₃,

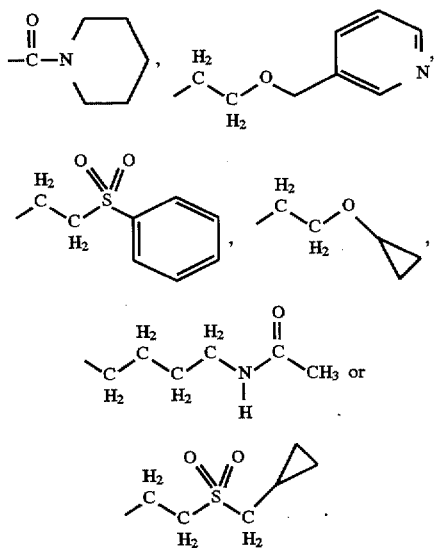

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following processes may be employed to produce compounds of the invention. Various intermediates in the processes described below can be produced by methods known in the art, see for example, U.S. Pat. No. 3,409,621, U.S. Pat. No. 5,089,496, WO89/10369, WO92/20681, WO93/02081, and WO95/00497; the disclosures of each being incorporated herein by reference thereto.

Compounds of the invention can be produced from ketones of Formula 3.0:

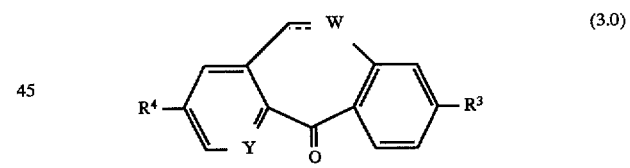

as described below. Compounds of Formula 3.0 are known or can be prepared by the procedures described in U.S. Pat. No. 5,089,496, WO89/10369, WO92/20681, and WO93/02081. For example, intramolecular cyclization of a nitrile of Formula 4.0:

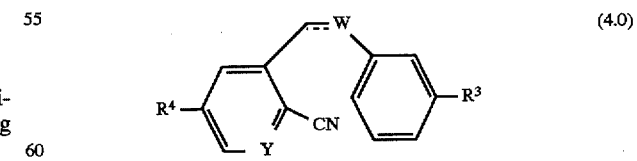

using a strong acid, such as CF₃SO₃H, at a temperature of about −15° to about 100° C., to form an imine intermediate which is hydrolyzed with water or aqueous acid to form the ketone of Formula 3.0

Alternatively, intramolecular Friedel-Crafts acylation of an acid chloride of Formula 5.0:

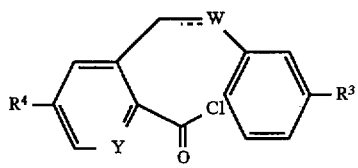

(5.0)

may also provide the desired ketone of Formula 3.0. The reaction may be carried out under the usual Friedel-Crafts conditions in an inert solvent and in the presence of a Lewis acid such as aluminium chloride. Acid 5 chlorides of Formula 5.0 can be obtained by the hydrolysis of a compound of Formula 4.0 to the corresponding carboxylic acid. Typically this can be done by heating with an aqueous acid (e.g., aqueous HCl), followed by conversion of the acid to the acid chloride of Formula 5.0 under standard conditions well known to those skilled in the art (e.g., by treating with $SOCl_2$ or oxalyl chloride).

Ketones of Formula 3.2 (i.e., compounds of Formula 3.0 wherein W is CH) can be prepared by heating a compound of Formula 3.1 (i.e., a compound of Formula 3.0 wherein W is $CH_2$) with $SeO_2$ in acetic acid.

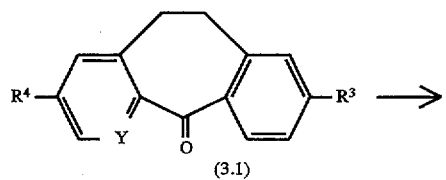

(3.1)

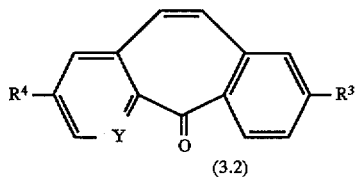

(3.2)

The ketone of Formula 3.0 is converted to the compound of Formula

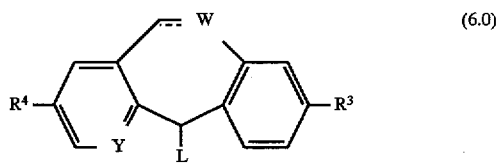

(6.0)

wherein L is Cl by a procedure analogous to that described in U.S. Pat. No. 3,409,621. For example, the ketone of Formula 3.0 is reduced to the corresponding alcohol using reagents such as sodium borohydride, and then the hydroxy group is converted to Cl by using reagents such as benzene and thionyl chloride. One skilled in the art can convert the hydroxy group to other leaving groups (e.g., Br, I, mesyloxy or tosyloxy). The compound of Formula 6.0 (wherein L is Cl) is reacted, at a temperature of about 25° to about 100° C., with a cyanide salt (e.g., CuCN AgCN or NaCN) in a suitable organic solvent, such as pyridine or benzene, to produce the nitrile of Formula 7.0.

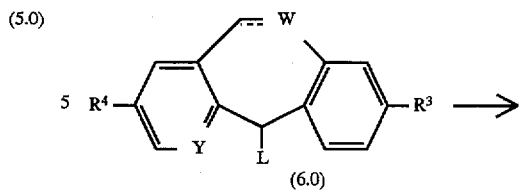

(6.0)

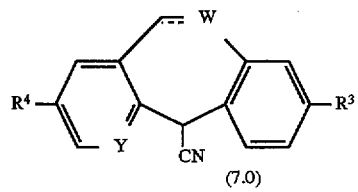

(7.0)

The nitrile of Formula 7.0 can be hydrolyzed to an acid (Formula 8.0 wherein $R^{20}$ is H), or an ester (Formula 8.0 wherein $R^{20}$ is —$CH_3$). Hydrolysis can be accomplished using an aqueous acid (e.g., HCl), or an acid (e.g., p-toluenesulfonic acid or $H_2SO_4$) and an alcohol (e.g., methanol or ethanol). The hydrolysis is carried out at a temperature of about 25° to about 80° C.

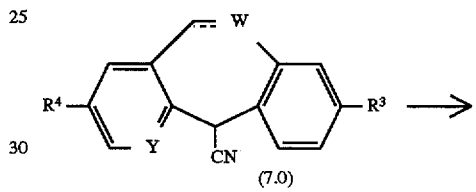

(7.0)

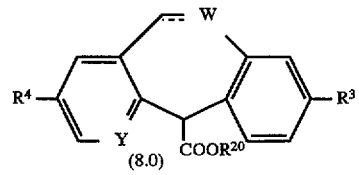

(8.0)

Alternatively, the compound of Formula 6.0 is reduced to the compound of formula 6.1 with a reducing agent, such as sodium borohydride, and a solvent, such as ethanol. The reduction is conducted at a temperature of about 25° C. The compound of Formula 6.0 can also be reduced to the compound of Formula 6.1 with zinc and acetic acid using a temperature of about 25° to about 100° C. (usually about 80° C.).

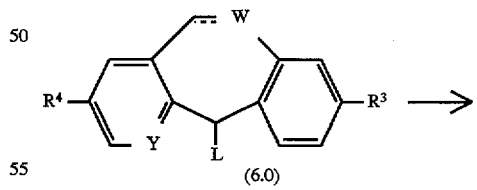

(6.0)

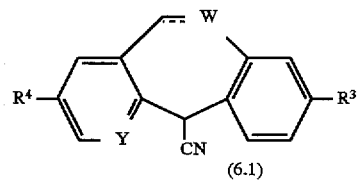

(6.1)

The compound of Formula 6.1 can be convened directly to a carboxylic acid of Formula 8.0 by treatment with a base such as n-butyl lithium followed by carbon dioxide.

The compound of Formula 8.0 is then reacted with a compound of Formula 9.0 to produce the compound of Formula 10.0. When the compound of Formula 8.0 is an acid (i.e., $R^{20}$ is H), the reaction is conducted with a coupling reagent (such as a carbodiimide, e.g., dicyclohexylcarbodiimide) in a suitable solvent (such as DMF, i.e., N,N-dimethylformamide) at room temperature. When the compound of Formula 8.0 is an ester (i.e., $R^{20}$ is —$CH_3$), the reaction is conducted in the presence of a base (e.g., triethylamine) in a suitable solvent (e.g., DMF) using elevated temperatures (e.g., about 100° C.).

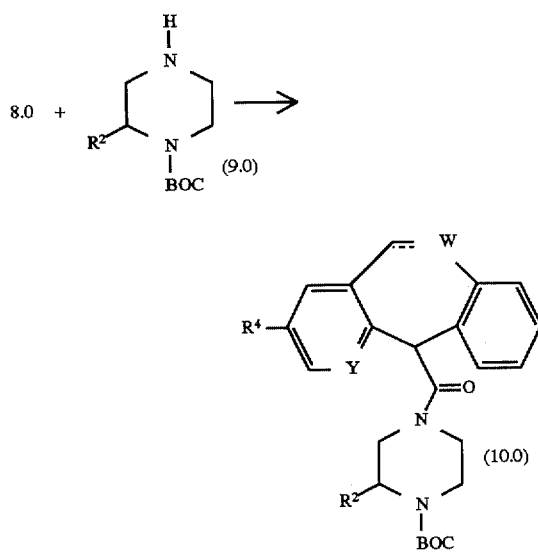

BOC is t-butyloxycarbonyl.

Those skilled in the art will appreciate that the compound of Formula 9.0 can exist as the two enantiomers

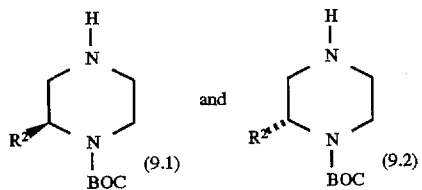

and preferably the enantiomer of Formula 9.1 is used to make the compounds of the invention. When the compound of Formula 9.1 is used compounds of formula 1.1 are obtained.

The compound of Formula 10.0 can be deprotected (i.e., the BOC group removed) by treatment with an acid (e.g., trifluoroacetic acid, or HCl-dioxane) to produce the compound of Formula 10.1:

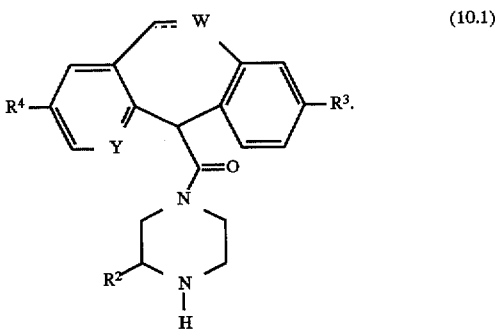

The compound of Formula 10.1 can be converted to the compound of Formula 1.1, wherein X is N, by acylation or reductive alkylation.

Alternatively, the compound of Formula 9.0 can be reacted with carbonyldiimiazole at about 0° C. using methylene chloride to produce a compound of Formula 11.0:

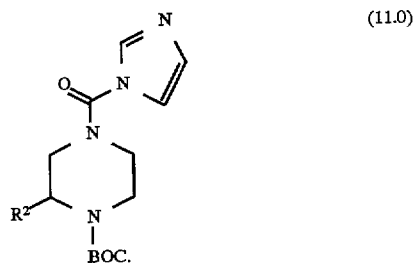

The compound of Formula 6.1 can be treated with butyl lithium, and then reacted with the compound of Formula 11.0 to produce the compound of Formula 10.0. The compound of Formula 10.0 can then be deprotected as described above to produce the compound of Formula 10.1.

SCHEME 1

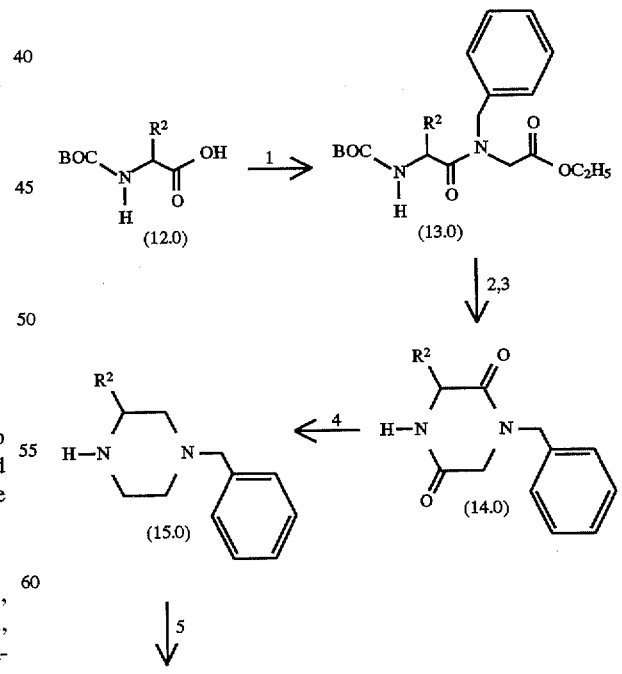

17

-continued
SCHEME 1

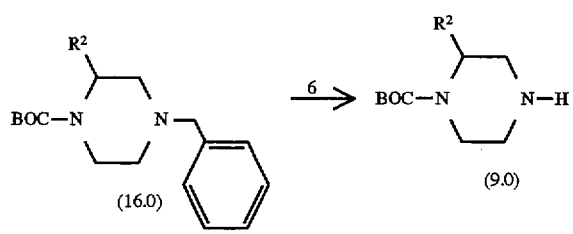

Scheme 1 describes the synthesis of 2-substituted piperazines wherein $R^2$ is H, alkyl, alkenyl, or alkynyl. Scheme 1 also describes the synthesis of 2-substituted piperazines wherein $R^2$ is alkyl, alkenyl, or alkynyl which are substituted with substituent groups (a), (b), (c), (d) and (g) as defined above, with the exception that $R^8$ and $R^9$ can not be a group that is substituted with —C(O)$R^{13}$ or —SO$_2$$R^{13}$. In Scheme 1, BOC-protected amino acids (12.0) are available commercially or can be made by procedures well known in the art. These amino acids can be coupled (step 1) to a commercially available N-benzylglycine ethyl ester using suitable coupling agents such as DCC (dicyclohexylcarbodiimide) or EDC (1-ethyl-3-(3-dimethylaminopropyl)carbodiimide hydrochloride) in suitable solvents (e.g., N,N-dimethylformamide, chloroform or methylene chloride) to produce a compound of Formula 13.0. Generally, this reaction is conducted at room temperature (i.e., about 25° C.). The BOC protecting group is removed (step 2) at room temperature with suitable reagents such as trifluoroacetic acid, or hydrogen chloride in chloroform or dioxane. The deprotected dipeptide is cyclized (step 3) under basic conditions to produce the compound of Formula 14.0. The compound of Formula 14.0 is then reduced (step 4) using LiAlH$_4$ in refluxing ether (diethyl ether) or THF to give the piperazine of Formula 15.0. The unsubstituted nitrogen of the piperazine of Formula 15.0 is protected (step 5) with a BOC group by procedures well known in the art to give the compound of Formula 16.0. The N-benzyl group is removed (step 6) by catalytic hydrogenation (e.g., using Pd/C and hydrogen gas under pressure of about 60 psi) to give the compound of Formula 9.0.

SCHEME 2

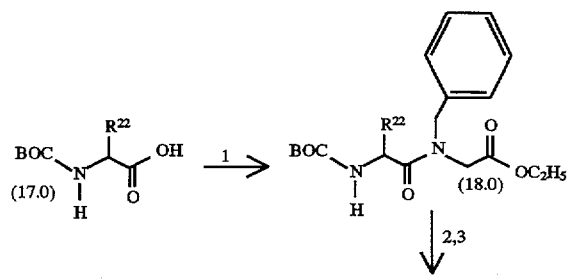

18

-continued
SCHEME 2

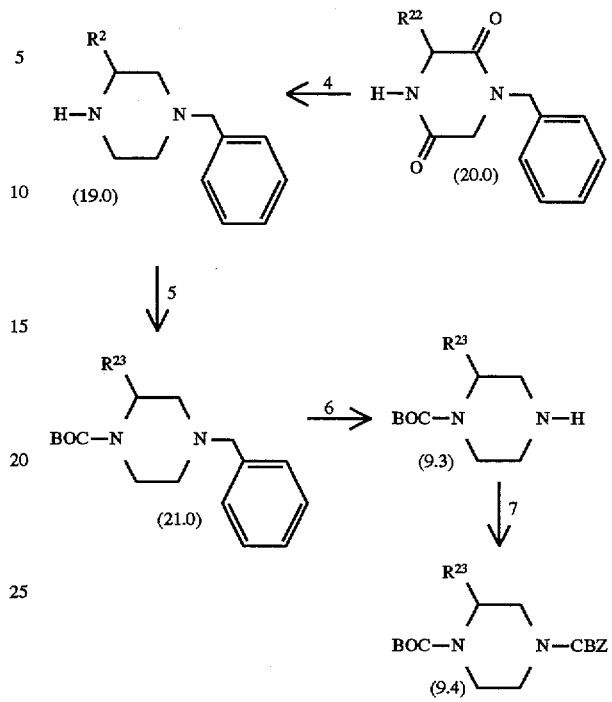

Compounds of Formula 9.0, wherein $R^2$ represents alkyl, alkenyl or alkynyl substituted with (a), (c), (d) or (g) groups wherein $R^8$ or $R^9$ are substituted with —C(O)$R^{13}$ or —S(O)$_2$$R^{13}$ are made according to the process of Scheme 2. Compounds of Formula 9.0, wherein $R^2$ represents —C(O)NR$^8$R$^9$ or —C(O)OR$^8$, or wherein $R^2$ represents alkyl, alkenyl or alkynyl substituted with a group (e), (f), or (h)–(o) are also made according to the process of Scheme 2. Compounds of Formula 17.0 (wherein $R^{22}$ is an alkyl, alkenyl or alkynyl group containing either a —OH group, a —COOH or its corresponding ester) are available commercially or can be made by procedures known in the art. In Scheme 2, the compound of Formula 17.0 is reacted according to the procedures described for Scheme 1 (steps 1 to 4) to produce a compound of Formula 19.0 wherein $R^{23}$ is a hydroxy substituted alkyl, alkenyl or alkynyl group. The compound of Formula 19.0 is then protected with a BOC group and then debenzylated according to the procedures in Scheme 1 (Steps 5 and 6) to produce a compound of Formula 9.3. The unsubstituted nitrogen of the compound of Formula 9.3 is protected (step 7) with a CBZ group (benzyloxycarbonyl) by procedures known in the art to produce the compound of Formula 9.4.

When $R^{23}$ is —CH$_2$OH, the hydroxy group can be oxidized to produce the corresponding carboxyl group- (COOH). This carboxyl group can them be esterified to produce compounds wherein $R^2$ is —C(O)OR$^8$, or the carboxyl group can be converted to amides to produce compounds wherein $R^2$ is —C(O)NR$^8$R$^9$ by procedures well known in the art.

To produce compounds of formula 9.0 in Scheme 2 wherein $R^2$ is a substituent other than —C(O)OR$^8$ or —C(O)NR$^8$R$^9$ (i.e., substituents (5) and (6)), the hydroxy group on $R^{23}$ can be converted to a leaving group, such as chloro, mesyloxy or tosyloxy, by techniques well known in the art. Then the leaving group can be displaced by various nucleophiles such as organometallics (to produce $R^2$ with an (a) substituent), thiols (to produce $R^2$ with a (d) substituent), sulfenyls (to produce $R^2$ with an (e) substituent), sulfinyls (to produce $R^2$ with an (f) or (m) substituent), amines (to produce $R^2$ with a (g) substituent), and alcohols (to produce $R^2$ with a (c) substituent). The hydroxy group on $R^{23}$ can also be acylated (to produce $R^2$ with a (j) or (k) substituent) or alkylated (to produce $R^2$ with a (c) substituent). When $R^{23}$ is alkyl having more than one carbon atom, or alkenyl or alkynyl, the hydroxy group can be oxidized, as discussed above, to produce the corresponding carboxyl group (i.e., substituent (o) wherein $R^8$ is H). This carboxyl group can be esterified to produce compounds wherein substituent (o) is —C(O)O$R^8$ wherein $R^8$ is other than H, or converted to amides to produce to produce $R^2$ with an (l) substituent by procedures well known in the art. When the leaving group is displaced by an amine (e.g., —N$R^8R^9$), the amine can then be converted to $R^2$ substituent groups (h), (i) or (n) by reacting the amine with an acyl halide (to produce $R^2$ with an (h) substituent), a carbamyl halide (to produce $R^2$ with an (i) substituent) or a sulfonyl halide (to produce $R^2$ with an (n) substituent) by procedures well known in the art.

The preparation of compounds of Formula 9.0 is described in WO95/00497, published Jan. 5, 1995, the disclosure of which has already been incorporated herein by reference thereto.

Compounds of Formula 1.0 wherein X is CH, and $R^2$ is alkyl, alkenyl or alkynyl, or $R^2$ is alkyl, alkenyl or alkynyl substituted with substituents (a), (b), (c), (d), or (g) with the exception that substituents $R^8$ or $R^9$ cannot have a halogen, —OH, —C(O)$R^{13}$ or —SO$_2R^{13}$ substituent, can be made from compounds of the Formula 22.0:

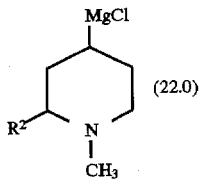

Compound 22.0 can be made according to the process:

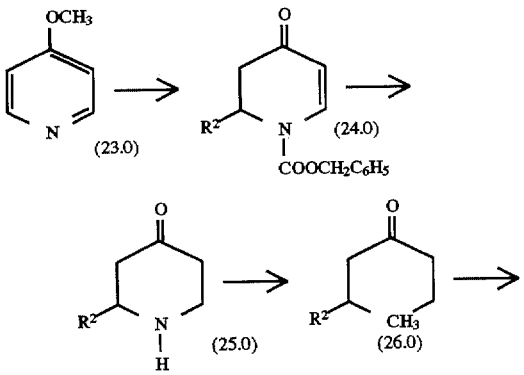

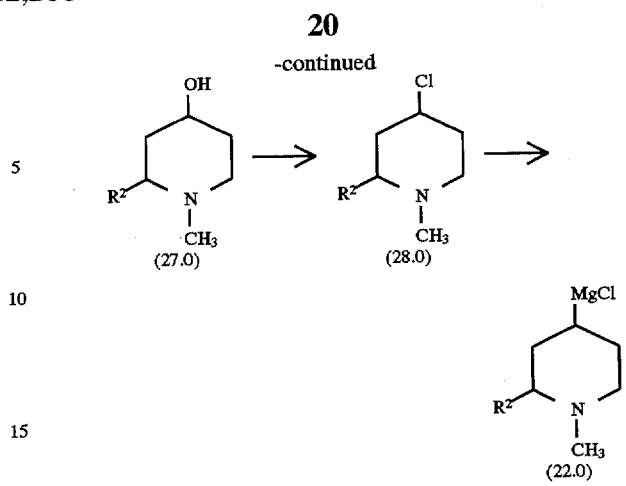

The substituted piperidines of Formula 22.0 may be prepared, as racemic mixtures, by essentially the same methods as described in D. L. Comins and J. D. Brown, Tetrahedron Letters, vol. 27 No. 38, pgs. 4549–4552, 1986. Thus, 4-methoxypyridine (23.0) may be converted using a variety of alkyl Grignard reagents (wherein $R^2$ is as illustrated below) and benzylchloroformate to the desired unsaturated ketopiperidines (24.0). Removal of the benzylcarbamoyl group with concomitant reduction of the double bond by catalytic hydrogenation yields the substituted ketopiperidines (25.0). Alternatively, the benzylcarbamoyl group can be removed with either base or acid followed by metal hydride reduction of the double bond to produce the compound of Formula 25.0. Alkylation of the compound of Formula 25.0 with a suitable alkyl iodide such as methyl iodide in the presence of sodium hydride gives the n-alkylketopiperidines (26.0). Reduction of the compound of Formula 26.0 with sodium borohydride affords the hydroxypiperidine of Formula 27.0. The compound of Formula 27.0 is reacted with a suitable chlorinating agent such as thionyl chloride to afford the 4-chloropiperidine of Formula 28.0 which may in turn be converted by reaction with magnesium into the compound of Formula 22.0.

The compound of Formula 22.0 is reacted with the compound of Formula 7.0, described above, in a suitable solvent such as diethyl ether or THF. The reaction is conducted at room temperature (about 25° C.) to about 50° C. This reaction is then followed by aqueous acid hydrolysis to yield ketones of the Formula:

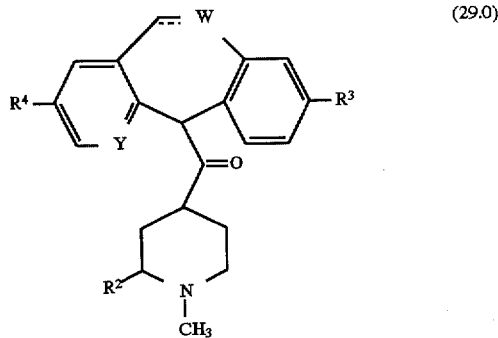

The N-methyl group on the piperidine ring can be converted to a carboethoxy group (—COOC$_2$H$_5$) by reaction with excess ethyl chloroformate in dry toluene containing triethylamine at a temperature of about 80° C. This procedure is similar to that described in U.S. Pat. Nos. 4,282,233 and 4,335,036. The carboethoxy group can be removed by either acid or base hydrolysis to give the compound of Formula 30.0:

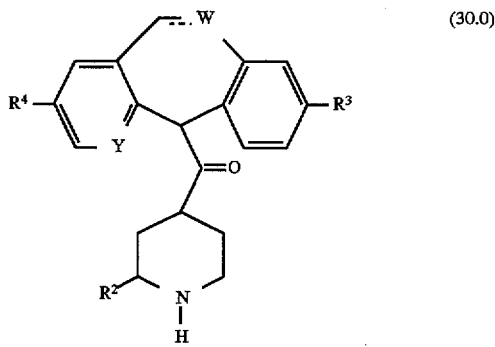

(30.0)

The compounds of Formula 30.0 are prepared as diasteromeric mixtures. Preferably, the diasteriomers are separated into single isomers by classical resolution methods or by chiral HPLC to yield:

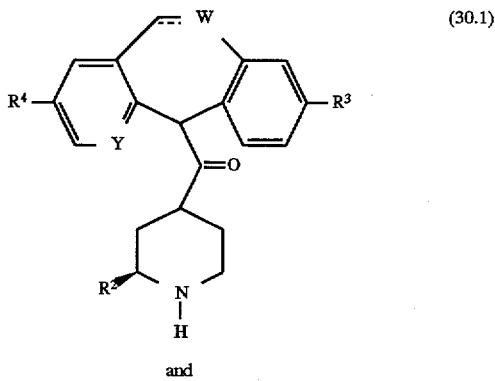

(30.1)

and (31.2)

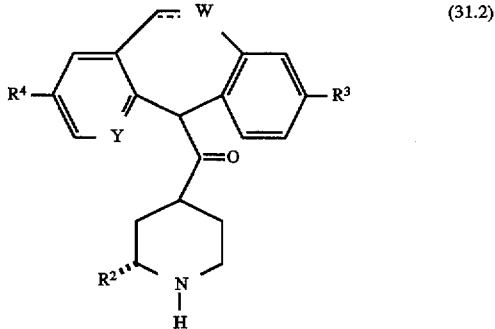

The compound of Formula 30.0, preferably 30.1, can be converted to the compound of Formula 1.0 (preferably 1.1), wherein X is CH, by acylation or inductive alkylation.

Acylation of the compounds of Formulas 10.1 and 30.0 can carried out by reacting the compound of Formula 10.0 or 30.0 with the corresponding carboxylic acid of the desired $R^1$ group with a coupling agent, such as a carbodiimide such as dicyclohexylcarbodiimide(DCC) or DEC (1-ethyl-3-(3-dimethylaminopropyl)carbodiimide). The acylation reaction can be carried out in a suitable organic solvent such as DMF, THF or methylene chloride at a temperature of about −10° to about 100° C., preferably at about 0° to about 50° C., and most preferably about room temperature. When the coupling reagent is DCC or DEC, the reaction is preferably conducted in the presence of HOBT.

Compounds of Formula 1.0, wherein $R^1$ is a substituent (a), (b), (c), (d), (e), (g), (i), (j), (k), (l), (z.1) or (z.2) can be made by reacting a compound of Formula 10.1 or 30.0 with $R^1$-L, wherein L is a leaving group such as Cl, Br, I, or a carboxylate (an anhydride). The reaction is out in the presence of a base, preferably a tetiary amine such as triethylamine or N-methyl morpholine.

Compounds of Formula 1.0, wherein $R^1$ is a substituent (m) to (q) can be made by reacting a compound of Formula 10.1 or 30.0 with a pyridyl isocyanate, pyridyl N-oxide isocyanate or piperidyl isocyanate corresponding to the pyridyl, pyridyl N-oxide or piperidyl moiety, respectively, of the substituent groups (m) to (q). The reaction is carried out in a suitable solvent such as DMF, THF or chloroform using techniques well known in the art. Alternatively, these ureas can be prepared by reacting a compound of Formula 10.1 or 30.0 with phosgene to form a chloroformate intermediate ($R^1$ is —(O)Cl). This chloroformate is generally not isolated, and is reacted with pyridyl amine, pyridyl N-oxide amine or piperidyl amine corresponding to the pyridyl, pyridyl N-oxide or piperidyl moiety, respectively, of the substituent groups (m) to (q) by techniques well known in the art.

Compounds of Formula 1.0 wherein $R^1$ is a substituent (r) to (v) can be made by reacting a compound of Formula 10.1 or 30.0 with a pyridyl chloroformate or piperidyl chloroformate; or, alternatively, reacting a compounds of Formulas 10.1 or 30.0 with excess phosgene and reacting the chloroformate thus produced with a hydroxypyridyl N-oxide. The reaction is carried out in a suitable solvent, such as dichloromethane, in the presence of a tertiary amine, such as pyridine, by techniques well known in the art.

Reductive alkylation of the compound of Formula 10.1 or 30.0 is accomplished by reacting the compound of Formula 10.1 or 30.0 with an aldehyde in DMF with a dehydrating agent such as molecular sieves at room temperature (about 25° C.). This reaction is followed by reduction of the intermediate imine with a reducing agent such as sodium cyanoborohydride or sodium triacetoxyborohydride. The reduction is usually carried out at room temperature in a suitable solvent such as DMF.

When compounds of Formulas 10.1 (X is N) or 30.0 (X is CH) are acylated to make the compounds of Formula 1.0 wherein $R^1$ is substituents (e) or (g), the protected compounds of Formulas 32.0 and 33.0, respectively are formed ($CPh_3$ represents triphenylmethyl). These protected compounds can be deprotected by using trifluoroacetic acid and triethylsilane to yield the compounds of Formulas 1.2 and 1.3, respectively. The compounds of Formulas 1.2 and 1.3 are isolated as the hydrochloride salt following the procedure described in Example 1E WO95/00497.

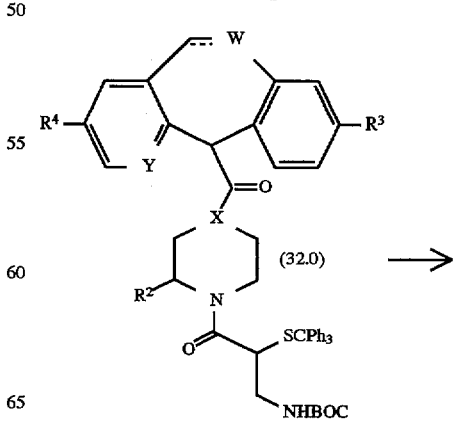

(32.0) →

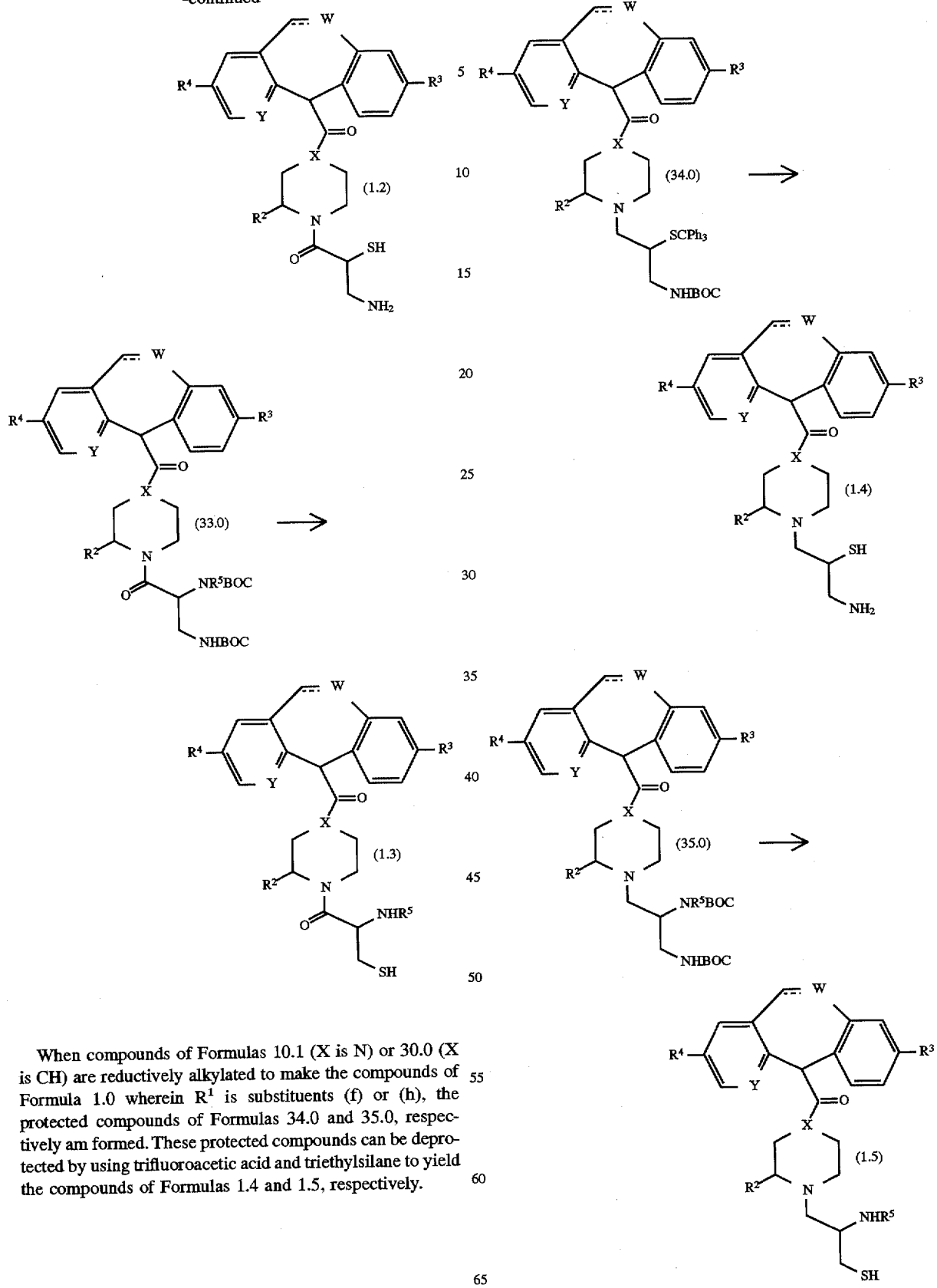
When compounds of Formulas 10.1 (X is N) or 30.0 (X is CH) are reductively alkylated to make the compounds of Formula 1.0 wherein $R^1$ is substituents (f) or (h), the protected compounds of Formulas 34.0 and 35.0, respectively am formed. These protected compounds can be deprotected by using trifluoroacetic acid and triethylsilane to yield the compounds of Formulas 1.4 and 1.5, respectively.

Certain compounds of Formula (1.0) can be convened to other compounds of the Formula (1.0) using standard reaction conditions. For example, compounds of the formula (1.0) wherein $R^2$ is —$CO_2H$, (i.e., —C(O)$OR^8$ and $R^8$ is H), can be prepared by ozonolysis of a compound of Formula (1.0) wherein $R^2$ is $CH_2$=CH—, followed by oxidation of the resulting aldehyde.

Compounds of the Formula (1.0) wherein $R^2$ is —C(O)$OR^8$, where $R^8$ is other than H, can be prepared from a compound of the formula (1.0) wherein $R^2$ is —$CO_2H$ by treating with $SOCl_2$ or oxalyl chloride, then with an alcohol of the formula $R^8OH$, wherein $R^8$ is as defined above. Similarly, compounds of formula (1.0) wherein $R^2$ is —C(O)$NR^8R^9$ can be prepared from a compound of the formula (1.0) wherein $R^2$ is —$CO_2H$ via essentially the same method but substituting and amine of the formula $R^8R^9NH$ for the alcohol $R^8OH$. Alternatively, compounds of Formula (1.0) wherein $R^2$ is —C(O)$NR^8R^9$ can be prepared by reacting a compound of the Formula (1.0) wherein $R^2$ is —$CO_2H$ with an amine $R^8R^9NH$ in the presence of a coupling agent, such as DCC or DEC.

In an analogous manner, compounds of Formula (1.0) wherein $R^2$ is alkyl substituted by a group of the formula —C(O)$OR^8$ or —C(O)$NR^8R^9$ can be prepared via substantially the same procedures as described above to form compounds wherein R is —$CO_2H$, —C(O)$OR^8$ or —C(O)$NR^8R^9$, by replacing the compound of Formula (1.0) wherein $R^2$ is $CH_2$=CH— with an appropriate alkenyl group, (i.e., a group of the formula —$(CH_2)_p$—CH=$CH_2$, wherein p is 1, 2, 3, 4, etc.).

Compounds of the Formula (1.0) wherein $R^2$ contains a substituent of formula —S(O)$_tR^8$, wherein t=1 or 2, can be prepared by oxidation of an analogous compound of the formula (1.0) wherein $R^2$ contains a substituent of formula —S(O)$_tR^8$, wherein t=0, using a suitable oxiding agent, such as a peracid, preferably MCPBA.

In the above processes, it is sometimes desirable and/or necessary to protect certain $R^1$, $R^2$, etc. groups during the reactions. Conventional protecting groups are operable as described in Greene, T. W., "Protective Groups In Organic Synthesis," John Wiley & Sons, New York, 1981, the disclosure of which is incorporated herein by reference thereto. For example, the groups listed in column 1 of Table 1 may be protected as indicated in column 2 of the table:

TABLE 1

| PROTECTED GROUP | |
|---|---|
| GROUP TO BE PROTECTED | 2. PROTECTED GROUP |
| —COOH | —COOalkyl, —COObenzyl, —COOphenyl, —C(OCH₂CH₂OCH₂)CH₃ |
| >NH | >NCOalkyl, >NCObenzyl, >NCOphenyl |

TABLE 1-continued

| PROTECTED GROUP | |
|---|---|
| GROUP TO BE PROTECTED | 2. PROTECTED GROUP |
| >CO | ketal/acetal protected forms |
| —OH | —O-THP, —OCH₂phenyl, —OCH₃, OSi(CH₃)₂(t-Bu) |
| —NHR, wherein R is any substituent of an amino group within the scope of the claims | —NR(THP-like), —NR—CO—CF₃, —NRCOCH₃, —NRCH₂phenyl |
| —$NH_2$ | phthalimide, —NH—C(O)—O(t-Bu) |

Compounds useful in this invention are exemplified by the following examples, which should not be construed as limiting the scope of the disclosure. Alternative mechanistic pathways and analogous structures within the scope of the invention may be apparent to those skilled in the art.

PREPARATIVE EXAMPLE 1

3-(1,1-DIMETHYL-1-ETHYL)-8-CHLORO-5,6-DIHYDRO-11H-BENZO(5,6)CYCLOHEPTA(1,2-b)PYRIDIN-11-ONE

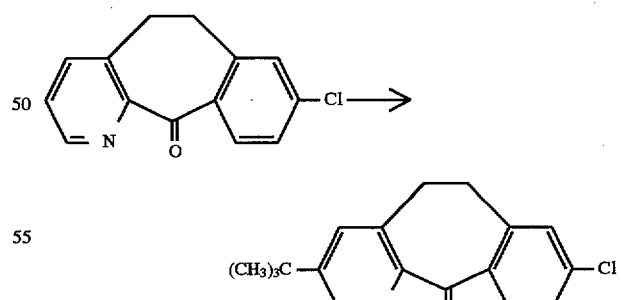

To a mixture of 20.05 grams (82.28 mmol) of 8-chloro-5,6-dihydro-11H-benzo[5,6]cyclohepta[1,2-b]pyridin-11-one in 400 ml of dry THF at −72° C. and under an atmosphere of nitrogen was added dropwise over 40 minutes 66.0 ml of 2.7M t-butyl magnesium chloride in THF. The reaction mixture was slowly warmed to room temperature and stirred overnight. The mixture was then poured into 10% aqueous ammonium chloride and extracted four times with CH₂Cl₂. The combined organic portions were dried over MgSO₄, filtered, and concentrated in vacuo to give the title compound, along with 8-chloro-11-(1,1-dimethyl-1-ethyl)-6,11-dihydro-5H-benzo[5,6]cyclohepta[1,2-b]pyridin-11-ol. These compounds were separated via flash chromatography to give the title compound, which was recrystallized from isopropyl ether to give 4.37 grams (18%) of the title compound as a white solid.

PREPARATIVE EXAMPLE 2

A. 8-CHLORO-6,11-DIHYDRO-11-HYDROXY-5H-BENZO[5,6]-CYCLOHEPTA[1,2-b]PYRIDINE

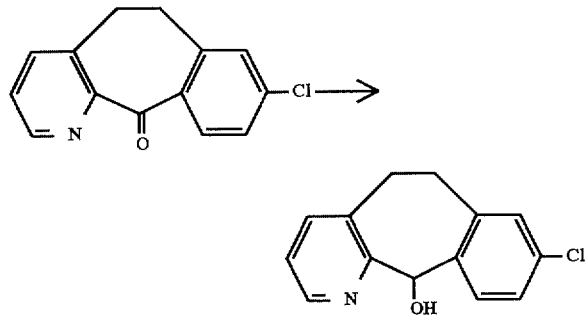

To a mixture of 25.03 g (103 mmol) of 8-chloro-5,6-dihydro-11H-benzo[5,6]cyclohepta[1,2-b]pyridin-11-one in 200 mL of methanol at room temperature and under a nitrogen atmosphere was added portionwise over a period of about 1 hour 4.82 g (124 mmol) of sodium borohydride. Occasional cooling with an ice bath was necessary at times during the addition in order to avoid excessive reflux. After 1.6 hours the mixture was poured into ice cold water and then extracted with ethyl acetate (3X). The combined organic portions were washed with brine, dried over MgSO₄, filtered, and concentrated in vacuo. The residue was recrystallized from hot isopropyl ether. The remaining filtrate was purified via flash chromatography (20% ethyl acetate in hexanes) to yield more product which solidified on standing. Both batches were combined to yield 20.41 g of the title compound as a white solid.

B. 8,11-DICHLORO-6,11-DIHYDRO-5H-BENZO[5,6]CYCLOHEPTA[1,2-b]PYRIDINE

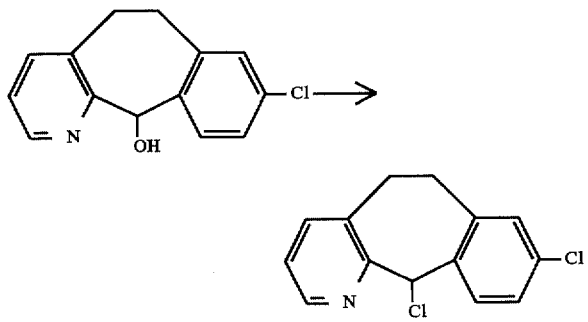

To a mixture of 13.3 g (54 mmol) of 8-chloro-6,11-dihydro-11-hydroxy-5H-benzo[5,6]cyclohepta[1,2-b]pyridine in 290 mL of toluene at −15° C. and under an atmosphere of nitrogen was added via syringe pump over a period of 1 hour 6.20 mL (85.7 mmol) of thionyl chloride. The extent of reaction was monitored by TLC (50% ethyl acetate in hexanes). When completed the mixture was poured into 300 mL of 1.0N aqueous NaOH and extracted with ethyl acetate (5X). The combined organic portions were washed with brine, dried over sodium sulfate, filtered, and concentrated in vacuo. The residue was taken up in ethyl acetate, quickly filtered through basic alumina, and concentrated again to yield a product which was triturated with pentane to yield 10.22 g of the title compound as a tan solid.

PREPARATIVE EXAMPLE 3

A. ETHYL 3-PYRIDYLACETIC ACID 1-N-OXIDE

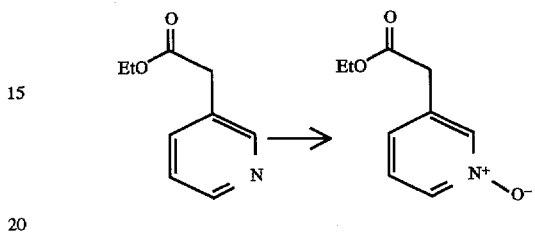

Ethyl 3-pyridylacetic acid (10 grams) (60.6 mmoles) was dissolved in dry CH₂Cl₂ (120 ml) and the solution was stirred at −18° C. for 30 minutes. MCPBA (31.34 grams) (181.6 mmoles) was added and the mixture was stirred at −18° C. for 1 hour and then at 25° C. for 87 hours. The reaction mixture was diluted with CH₂Cl₂ and washed with saturated aqueous sodium bicarbonate and then water. The CH₂Cl₂ was then dried (magnesium sulphate), filtered and evaporated to dryness. The residue was chromatographed on silica gel using 3% (10% concentrated ammonium hydroxide in methanol)-CH₂Cl₂ as the eluant to give the title compound (Yield: 8.45 grams, 77%, MH⁺ 182).

B. 3-PYRIDYLACETIC ACID 1-N-OXIDE

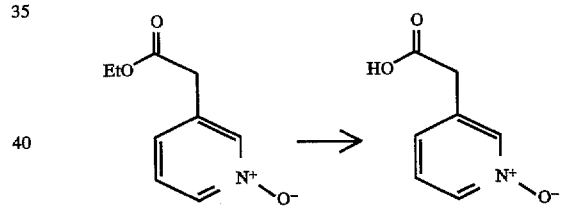

Ethyl-3-pyridylacetic acid 1-N-oxide (0.2747 grams) (1.5 mmoles) was dissolved in ethanol (200 proof) (1.22 ml.) and a 1M solution of LiOH in water (3.64 ml.) (3.0 mmoles) was added and the mixture was stirred at 25° C. for 4 hours. 1N HCl (4.28 ml.) was added and the mixture was pumped down to dryness on a rotary evaporator to give the title compound (Yield: 0.2931 grams, 100%).

PREPARATIVE EXAMPLE 4

4-ETHOXYCARBONYLAMINOPYRIDINE

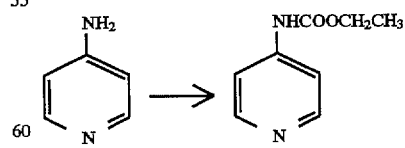

4-Aminopyridine (17.34 grams) (184.3) was dissolved in dry pyridine (217 ml.) and cooled to 0° C. over 30 minutes. Ethyl chloroformate (17.2 ml.) (180.7 mmoles) was added and the solution was stirred at 0° C. for 1 hour and then at 25° C. for 40 hours. The mixture was diluted with CH₂Cl₂ and washed with saturated aqueous NaHCO₃ and water. The CH₂Cl₂ was dried (MgSO₄), filtered and evaporated to dryness. The residue was chromatographed on silica gel using 2%(10% saturated NH₄OH in MeOH)—CH₂Cl₂ to give the title compound (Yield: 10 grams, 33%, M⁺ 166).

By using essentially the same procedure, with the exception that

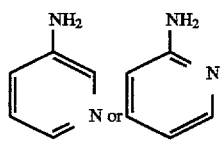

was used instead of 4-aminopyridine, the compound

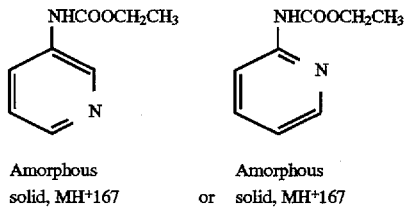

Amorphous solid, MH⁺167 or Amorphous solid, MH⁺167 was obtained, respectively.

PREPARATIVE EXAMPLE 5
A. PIPERIDINE-4-ACETIC ACID

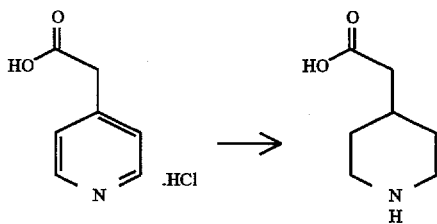

4-Pyridylacetic acid (7 grams) (40.4 mmoles) was hydrogenated in water (100 ml) using 10% Pd-C at 40 psi at 25° C. for 24 hours. The catalyst was filtered off and washed with water. The aqueous solution was shaken with BioRad AG1×8 resin (OH⁻ form) (23 ml bed) and after 5 minutes the resin was filtered off and washed with water. The aqueous solution was evaporated to give the title compound (Yield: 5.2 grams, MH⁺ 144).

B. 1-N-ACETYL-4-PIPERIDINYLACETIC ACID

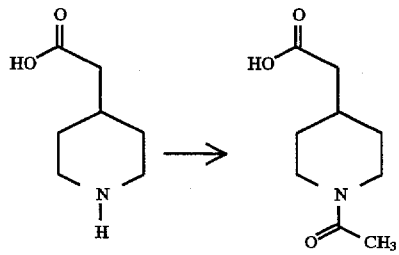

4-Piperidinylacetic acid (5 grams) (35.0 mmoles) was reacted with acetic anhydride (10.7 grams) (105.0 mmoles) in MeOH (100 ml.) and the mixture was stirred at 25° C. for 24 hours. The mixture was evaporated to dryness and the residue was azeotroped with toluene to give the title compound (Yield: 6.4 grams, 99%, MH⁺ 185).

C. 1-N-METHYL-4-PIPERIDINYLACETIC ACID

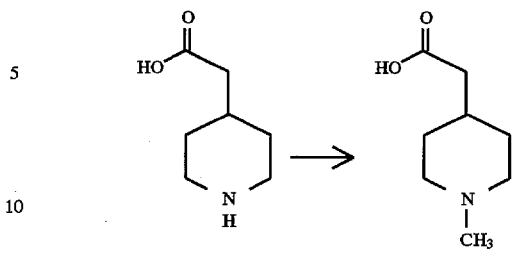

4-Piperidinylacetic acid (4 grams) (28.0 mmoles) from Preparative Example 5A was dissolved in water (50 ml) and 37% formalin (2.72 ml) (33.6 mmoles) was added. The mixture was hydrogenated over 10% Pd-C t 55 psi at 25° C. for 68 hours. The catalyst was filtered off and washed with water. The combined filtrates were evaporated to dryness to give the title compound (MH+158).

D. 1-N-tert-BUTOXYCARBONYLPIPERIDINYL-4-ACETIC ACID

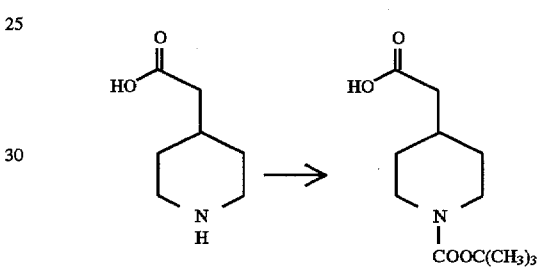

4-Piperidinylacetic acid (41.24 grams) (288.4 mmoles) from Preparative Example 5A was dissolved in THF-water (1:1) (400 ml) and di-tert-butyldicarbonate (69.14 grams) (317.3 mmoles) and NaOH (11.52 grams) (288.4 mmoles) were added. The mixture was stirred at 25° C. for hours. The solution was then eluted through a bed of washed BioRad 50WX4 (RSO3H resin) (150 ml bed) and the resin was eluted with a 1:1 mixture of THF and water. The eluate was evaporated to dryness to give the title compound (Yield: 53.0 grams, 76%).

PREPARATIVE EXAMPLE 6
A. 3-PIPERIDINYLACETIC ACID

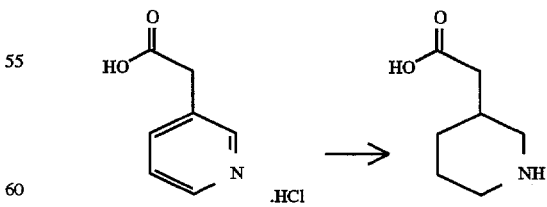

3-Pyridylacetic acid hydrochloride (13 grams) (74.9 mmoles) was hydrogenated as described in Preparative Example 5A to give a mixture of unreacted 3-pyridylacetic acid and the title compound (76:24) (8.63 grams, MH⁺ 144).

B. 1-N-ACETYL-3-PIPERIDINYLACETIC ACID

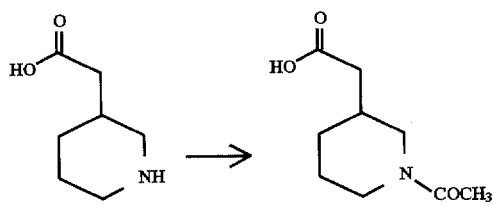

The mixture of compounds from Preparative Example 6A (8.56 grams) were reacted with acetic anhydride (8.56 grams) as described in Preparative Example 5B and the crude mixture of products was diluted in methanol (60 ml) and passed over a bed of BioRad AG50WX4 resin (RSO$_3$H) and the latter was eluted with methanol. The eluates were evaporated to dryness to give the title compound (Yield: 1.23 grams, MH$^+$ 186).

C. 1-N-METHYL-3-PIPERIDINYLACETIC ACID

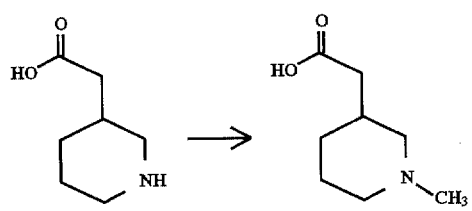

The mixture of compounds from Preparative Example 6A (4 grams) and 37% formalin (2.72 ml.) were hydrogenated as described in Preparative Example 5C to give the title compound (MH$^+$ 158).

PREPARATIVE EXAMPLE 7

3-BROMO-8-CHLORO-5,6-DIHYDRO-11H-BENZO[5.6]-CYCLOHEPTA[1.2-b]PYRIDIN-11-ONE

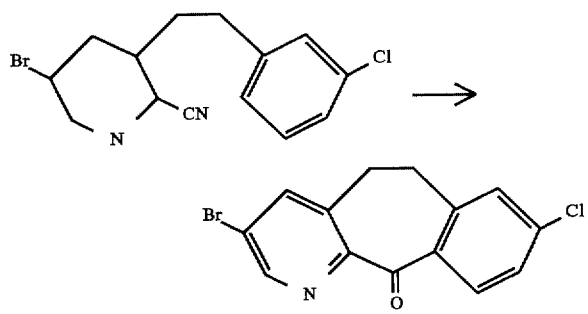

Cyclize 3-[2-(3-chlorophenyl)ethyl]-4-bromo-2-pyridine carbonitrile (10.7 g, 32.8 mmol) in triflic acid (82 mL) at 60° C. for 2 hours and then at room temperature for 2 hours. Add 80 mL of 5N HCl carefully, then reflux in an oil bath (120° C.) for 30 minutes. Cool the solution and pour into ice and basify with 25% NaOH solution. Extract the product with CH$_2$Cl$_2$ and wash with brine. Dry the organic layer with Na$_2$SO$_4$, filter and remove the solvent to give crude product (10.4 g). Purify the crude product with flash chromatography on silica gel and elute with 15% ethyl acetate-hexane to give the title compound as a white solid (9 g, 27.95 mmol, Yield 85.2% MH$^+$ 322).

PREPARATIVE EXAMPLE 8

3-PYRIDYLISOCYANATE, HYDROCHLORIDE

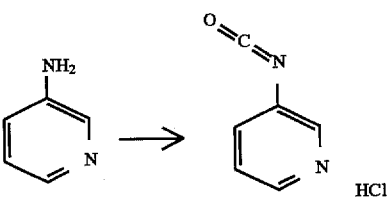

A 1.93 solution of phosgene in toluene (20%) (584 mL) was diluted with dry CH$_2$Cl$_2$ (1 L) and the mixture was stirred at 0° C. under nitrogen atmosphere. A solution of 3-aminopyridine (21.1 grams) and dry pyridine (19 mL) dissolved in dry CH$_2$Cl$_2$ (600 mL) was added dropwise to the stirred solution at 0° C. over a period of 5.5 hours. The mixture was stirred at 0°–25° C. for an additional 48 hours. A stream of nitrogen was passed through the solution to remove most of the phosgene and the solution was then evaporated until almost all of the solvent was removed to give the title compound which was then taken up in dry pyridine (850 mL) to give a stock solution of the title compound.

PREPARATIVE EXAMPLE 9

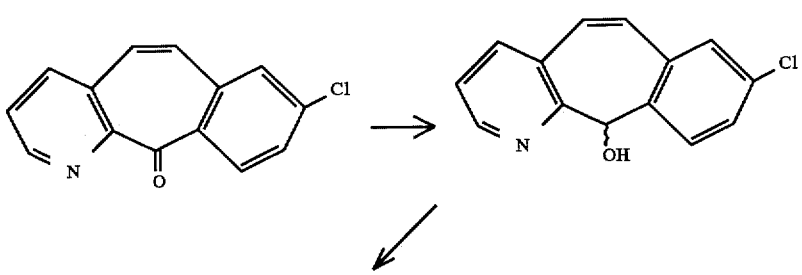

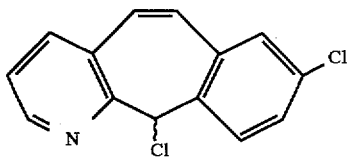

The preparation of the starting material for this reaction was described in The Journal of Organic Chemistry, 1990, 55, pp. 3341–3350 by Piwinski, J. J., et al. By substituting in Preparative Example 2A, 8-chloro-11H-benzo[5,6]cyclohepta[1,2-b]pyridin-11 -one (11.53 g) (47.71 mmoles) for 8-chloro-5,6-dihydro-11H-benzo[5,6]cyclohepta[1,2-b] pyridin-11-one and employing basically the same methods as steps A and B of Preparative Example 2, one obtains 11.53 g (36%) of the title compound (MH$^+$ 312).

PREPARATIVE EXAMPLE 10

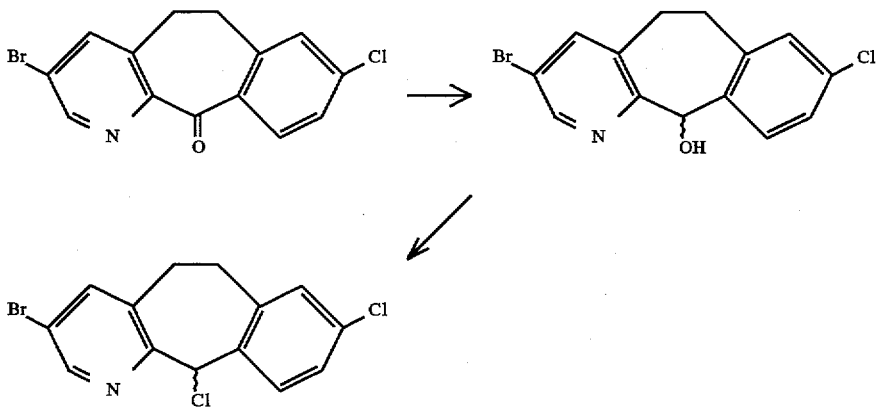

By substituting in Preparative Example 2A, 3-bromo-8-chloro-11-(1-15 piperazinyl) -5,6-dihydro- 11H-benzo[5,6] cyclohepta[1,2-b]pyridin-11-one (1.5 g, 4.65 mmoles) (Preparative Example 7A) for 8-chloro-5,6-dihydro-11H-benzo[5,6]cyclohepta[1,2-b]pyridin-11-one and using the same methods as described in steps A and B of Preparative Example 2, one obtains the title compound (1.31 g, 72%, MH$^+$ 392).

PREPARATIVE EXAMPLE 11

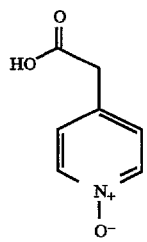

Step A:

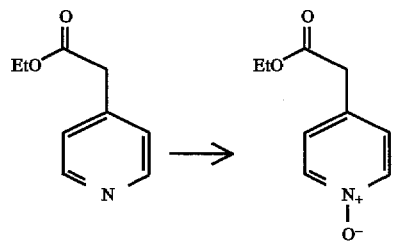

Combine 10 g (60.5 mmol) of ethyl 4-pyridylacetate and 120 mL of dry $CH_2Cl_2$ at –20° C., add 10.45 g (60.5 mmol) of MCPBA and stir at –20° C. for 1 hour and then at 25° C. for 67 hours. Add an additional 3.48 g (20.2 mmoles) of MCPBA and stir at 25° C. for 24 hours. Dilute with $CH_2Cl_2$ and wash with saturated $NaHCO_3$ (aqueous) and then water. Dry over $MgSO_4$, concentrate in vacuo to a residue, and chromatograph (silica gel, 2%–5.5% (10% $NH_4OH$ in MeOH)/$CH_2Cl_2$) to give 8.12 g of the product compound (Et represents —$C_2H_5$ in the formula). Mass Spec.: MH$^+$= 182.15

Step B:

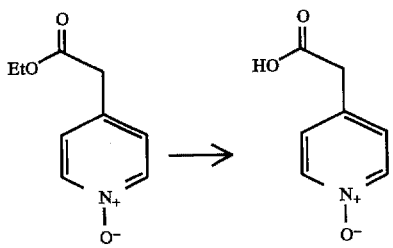

Combine 3.5 g (19.3 mmol) of the product of Step A, 17.5 mL of ethanol and 96.6 mL of 10% NaOH (aqueous) and heat the mixture at 67° C. for 2 hours. Add 2N HCl (aqueous) to adjust to pH=2.37 and concentrate in vacuo to a residue. Add 200 mL of dry ethanol, filter through celite® and wash the filter cake with dry EtOH (2×50 ml). Concentrate the combined filtrates in vacuo to give 2.43 g of the title compound.

PREPARATIVE EXAMPLE 12

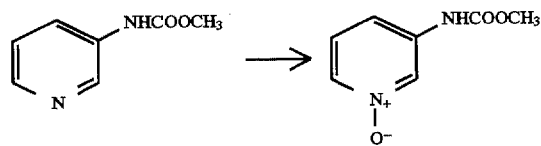

Combine 10 g (65.7 mmol) of 3-methoxycarbonylaminopyridine and 150 mL of $CH_2Cl_2$, cool to 0° C. and slowly add (dropwise) a solution of 13.61 g (78.84 mmol) of MCPBA in 120 mL of $CH_2Cl_2$ at 0° C. over a period of 1 hour. Stir the mixture at 25° C. for 5 days, then wash with saturated $NaHCO_3$ (aqueous), then water and dry over $MgSO_4$. Concentrate in vacuo to a residue and chromatograph (silica gel, 2%–5% (10% $NH_4OH$ in MeOH) /$CH_2Cl_2$) to give the product compound. Mass Spec.: $MH^+$= 169

PREPARATIVE EXAMPLE 13

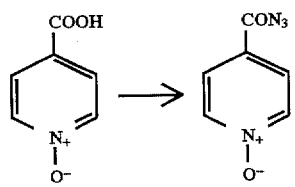

Combine 5 g (36.0 mmol) of isonicotinic acid 1-N-oxide and 150 mL of anhydrous DMF, add 5.5 mL (39.6 mmol) of triethylamine and stir at 0° C. for 0.5 hours. Slowly add (dropwise) 8.5 mL (39.6 mmol) of diphenylphosphoryl azide at 0° C. over 10 minutes, stir at 0° C. for 1 hour and then at 25° C. for 24 hours (as generally described in Pavia, et al., *Journal of Medicinal Chemistry*, 33, 854–861 (1990). Concentrate in vacuo to a residue and chromatograph (silica gel, 0.5%–1% MeOH/$CH_2Cl_2$) to give 5.9 g of the product compound.

Using nicotinic acid 1-N-oxide and substantially the same procedure as described for Preparative Example 13 the following compound was prepared:

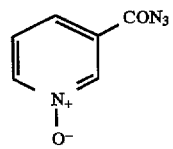

PREPARATIVE EXAMPLE 15

Step A:

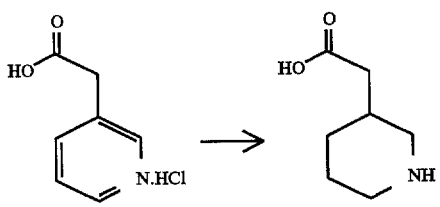

Hydrogenate 25 g (144 mmol) of 3-pyridylacetic acid hydrochloride for 144 hours using the procedure described in Preparative Example 5A to give 20 g of the product compound. Mass Spec.: $MH^+$=144.

Step B:

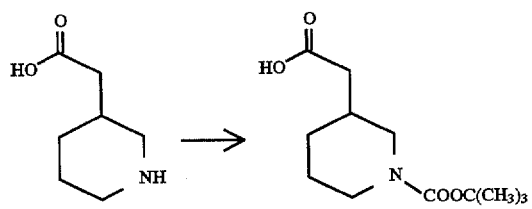

React 12 g (83.8 mmol) of the product of Step B for 148 hours using the procedure described in Preparative Example 5D, to give 17.5 g of the product compound. Mass Spec.: $MH^+$=244.25

PREPARATIVE EXAMPLE 15

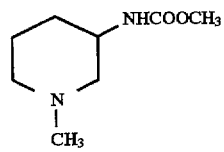

Combine 25 g (164.4 mmol) of methyl 3-pyridylcarbamate and 163.3 mL of 1N HCl (aqueous), stir until all of the solid dissolves, then hydrogenate over 10% Pd/C at 25° C. at 55 psi for 220 hours. Filter, wash the solids with water and treat the combined filtrates with 150 mL of BioRad AG1X8 ion exchange resin ($OH^-$). Filter, wash the resin with water and concentrate the filtrate to a volume of 100 mL. Add 16.43 mL (197.3 mmol) of 37% formalin and hydrogenate over 10% Pd/C at 25° C. at 55 psi for 89 hours. Filter, wash the solids with water and concentrate in vacuo to give 24.3 g of the title compound. Mass Spec.: $MH^+$= 173.2

PREPARATIVE EXAMPLE 16

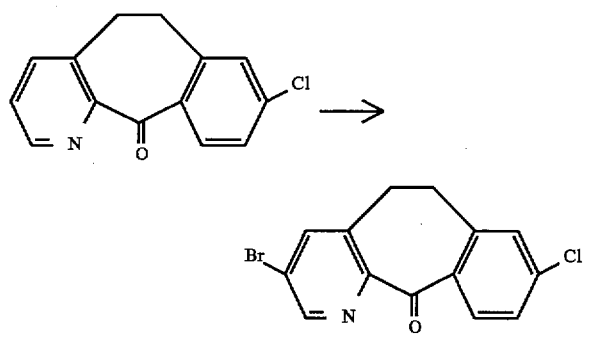

Cool 50.0 g (20.5 mmol) of 8-chloro-5,6-dihydro-11H-benzo[5,6]cyclohepta[1,2-b]pyridin-11-one to 0° C., slowly add 75 mL (93.69 mmol) of sulfur monochloride over 20 minutes, then slowly add 25 mL (48.59 mmol) of $Br_2$ over 15. Heat at 95° C. for 20 hour, add 12.5 mL (24.3 mmol) of $Br_2$ and heat for a another 24 hours. Cool the mixture, and slowly add to a mixture of $CH_2Cl_2$ and 1N NaOH (aqueous) at 0° C. Wash the organic phase with water, dry over $MgSO_4$ and concentrate in vacuo to a residue. Chromatograph the residue (silica gel, 500 mL $CH_2Cl_2$ then 0.2%–5% (10% $NH_4OH$ in MeOH)/$CH_2Cl_2$), then chromatograph again (silica gel, 3%–8.5% EtOAc/hexane) to give 8.66 g of the product compound. Mass Spec.: $MH^+=322$

PREPARATIVE EXAMPLE 17

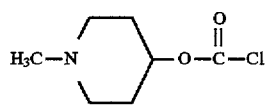

Combine 10 mL of dry $CH_2Cl_2$ and 914.6 mL (28.1 mmol) of a 1.93M solution of phosgene in toluene, cool to 0° C. and slowly add (dropwise) a solution of 0.6484 g (5.62 mmol) of 4-hydroxy-1-N-methylpiperidine, 1.214 mL (15 mmol) of pyridine and 10 mL of dry $CH_2Cl_2$ over 10 minutes, then stir at 0° to 25° C. for 2 hours. Purge excess phosgene with $N_2$ then concentrate in vacuo to give the title compound.

EXAMPLE 1

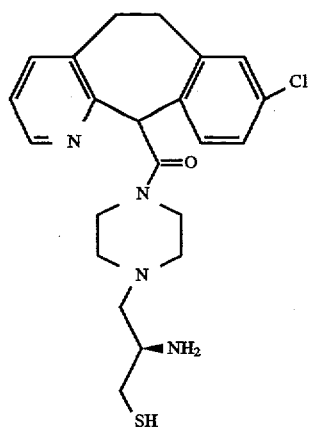

Step A:

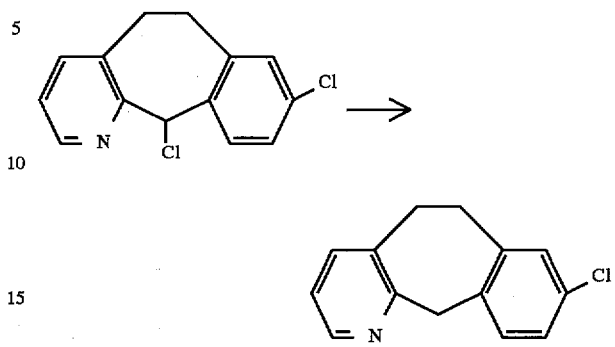

Following the procedure of Villani et al., J. Med. Chem. 15, 750 (1972), the product of Preparative Example 2 was dissolved in acetic acid and excess zinc was added. This mixture was heated for two hours at 80° C. The reaction mixture was filtered and concentrated under vacuo. Aqueous sodium bicarbonate was added and the mixture was extracted with ethyl acetate. The organic layer was washed with water and dried over magnesium sulfate, filtered and concentrated under vacuo. The concentrated material was chromatographed on silica gel using ethyl acetate-hexane to obtain the product.

Step B:

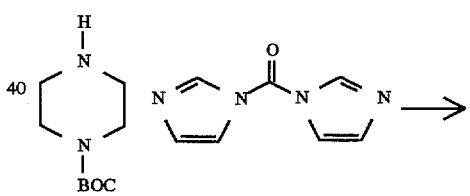

Piperazine protected with a BOC group (commercially available) was dissolved in methylene chloride and 1.2 equivalents of carbonyldiimidazole was added at 0° C. and the mixture was stirred for 15 minutes. Sodium chloride solution was added and the mixture was extracted with methylene chloride. The organic layer was dried over magnesium sulfate, filtered and concentrated under vacuo to obtain the product.

Step C:

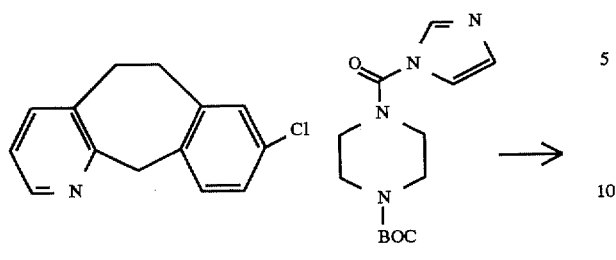

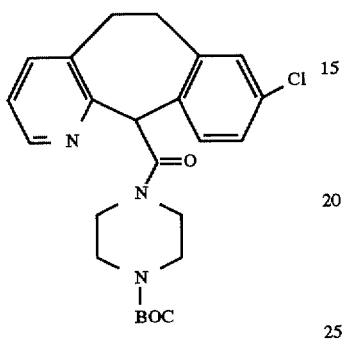

The product of Step A was dissolved in tetrahydrofuran and cooled to −78° C. One equivalent of butyl lithium was added and the mixture was stirred for 10 minutes. One equivalent of the product of Step B in tetrahydrofuran was added and the mixture was stirred for 1 hour at −78° C., and then at 25° C. for 18 hours. Water was added and the mixture was extracted with ethyl acetate, the organic layer was dried over magnesium sulfate and concentrated under vacuo. The concentrated material was chromatographed on silica gel using ethyl acetate-hexane to give the product as a tan solid, M+1=442.

Step D:

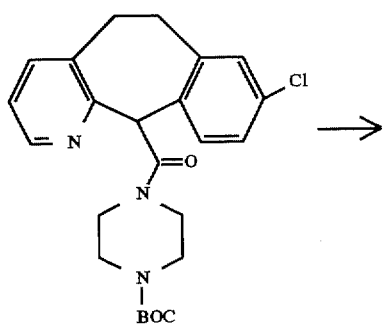

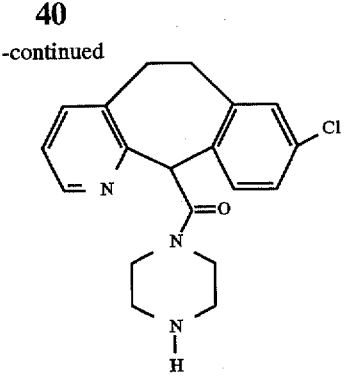

The product of Step C was dissolved in HCl-Dioxane and stirred until reaction was completed (about 1 hour). Concentration in vacuo gave the product.

Step E:

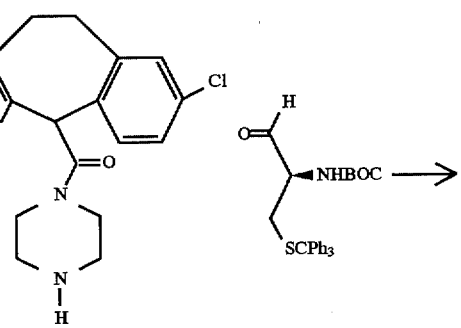

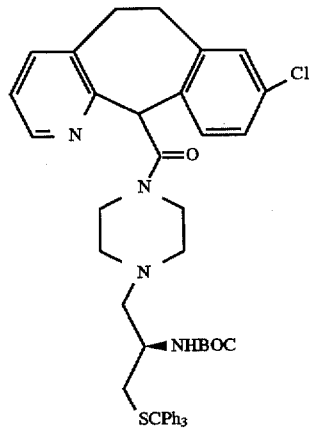

The product of Step D was dissolved in N,N-dimethylformamide and the pH was adjusted to 6 with triethylamine. Sodium triacetoxyborohydride, 1.25 equivalents, and crushed 4A molecular sieves were added to the solution. The resulting mixture was cooled to 0° C. under nitrogen and 1.5 equivalents of the reactant aldehyde (see Example 1 on page 45 of WO95/00497) in N,N-dimethylformamide was added dropwise. After addition was completed, the mixture was stirred at 0° C. for 2½ hours. The mixture was then diluted with ethyl acetate, filtered, and washed with sodium bicarbonate solution. The organic layer was dried over magnesium sulfate, filtered and concentrated under vacuo. The concentrated material was chromatographed on silica gel using ethyl acetate-hexane to give a white solid. M+1 =772.

Step F:

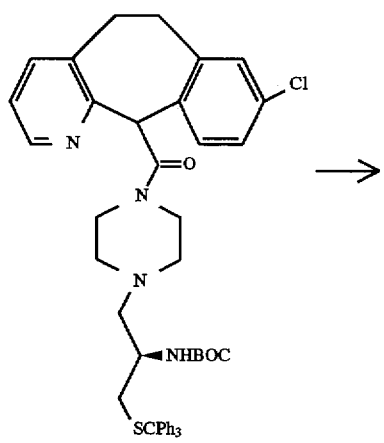

The product of Step E was treated with 1N HCl in acetic acid at room temperature for ½ hour, then at 47° C. for 15 minutes, cooled to 20° C. and treated with triethylsilane for ½ hour. The hydrochloride of the title compound was isolated as a white powder by diluting the reaction mixture with ethyl acetate followed by centrifugation. M+1 =431.

EXAMPLE 2

If one were to follow the procedures described in Steps A and B then one would obtain a compound of the formula:

Step A:

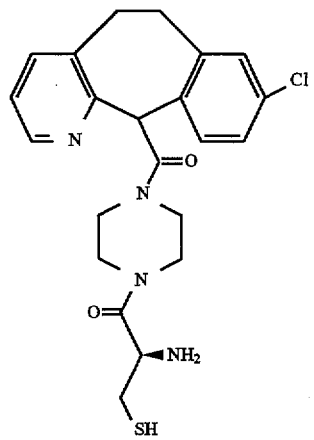

Dissolve the product of Example 1, Step D, in N,N-dimethylformamide and add 1 equivalent of the reactant carboxylic acid (commercially available), 1 equivalent of 1-hydroxybenzotriazole, 1 equivalent of 1-ethyl-3-(3-dimethylaminopropyl)carbodiimide hydrochloride (DEC) and 1 equivalent of triethylamine. Stir until reaction is complete, about 18 hours. Concentrate in vacuo. Chromatograph on silica gel using ethyl acetate-hexane to obtain the product.

Step B:

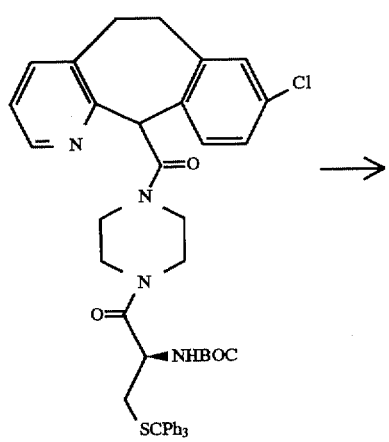

→

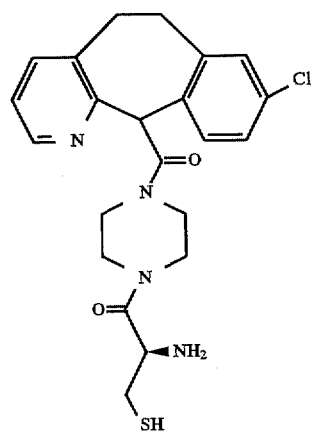

React and purify as in Example 1, Step F, to obtain the product.

EXAMPLE 3

If one were to follow the procedures described in Steps A to F then one would obtain a compound of the formula:

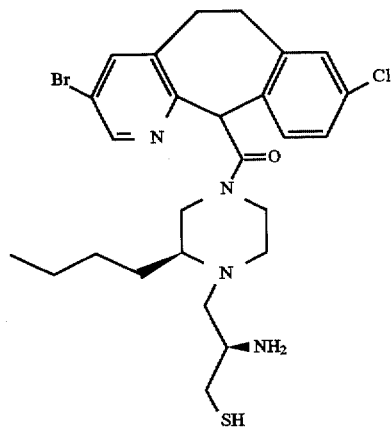

Step A:

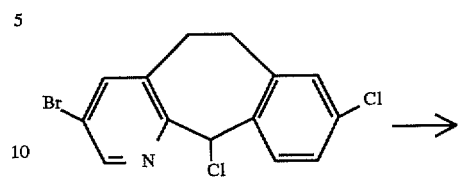

→

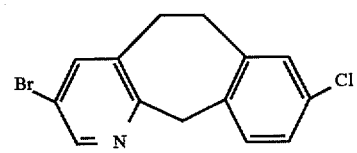

Follow the procedure set forth in Example 1, Step A, using the product of Preparative Example 10 to obtain the product.

Step B:

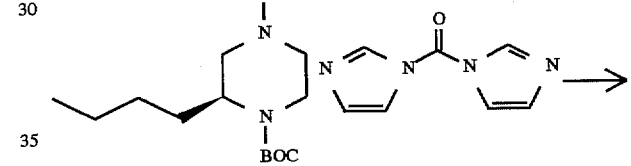

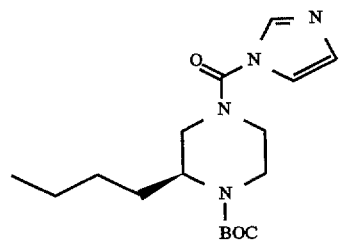

Follow the procedure of Example 1, Step B, using the product of Example 3, Step B, to obtain the product.

Step C:
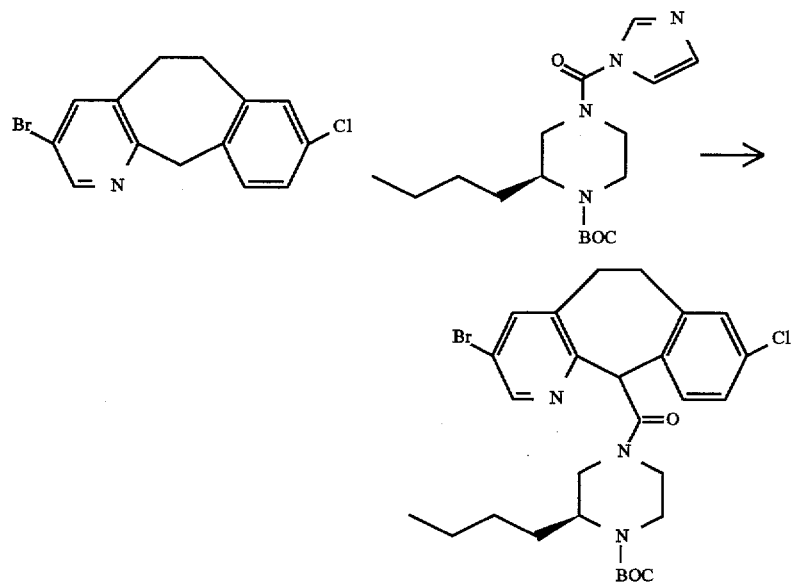
Step D:
Follow the procedure of Example 1, Step C, using the products of Example 3, Steps A and B, to obtain the product.
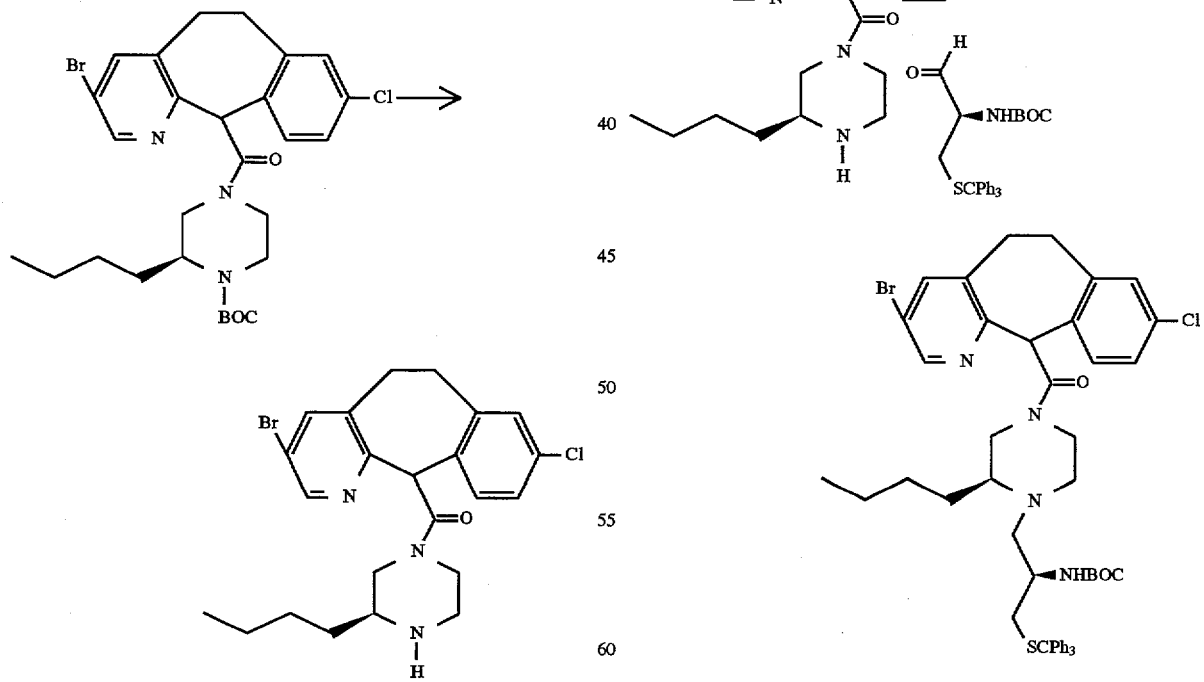
Follow the procedure of Example 1, Step D, using the product of Example 3, Step C, to obtain the product.
Follow the procedure of Example 1, Step E, using the product of Example 3, Step D, and the aldehyde to give the product.

Step F:

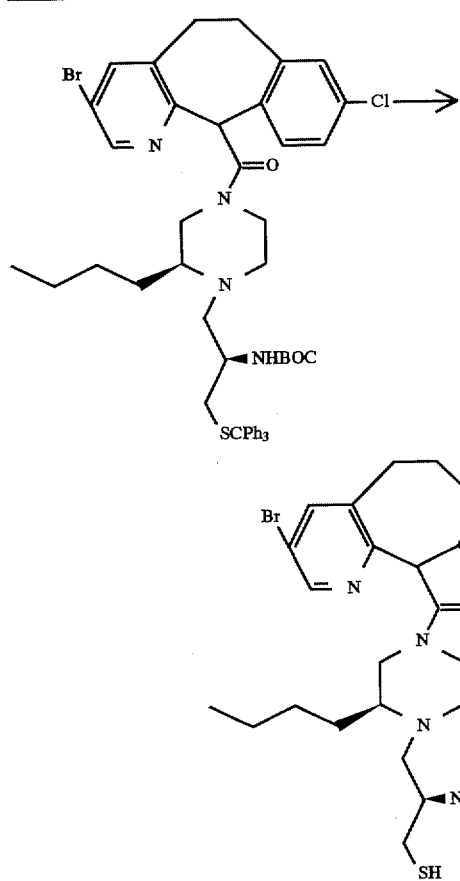

Follow the procedure of Example 1, Step F, using the product of Example 3, Step E, to give the product.

EXAMPLE 4

If one were to follow the procedures described in Steps A to E then one would obtain a compound of the formula:

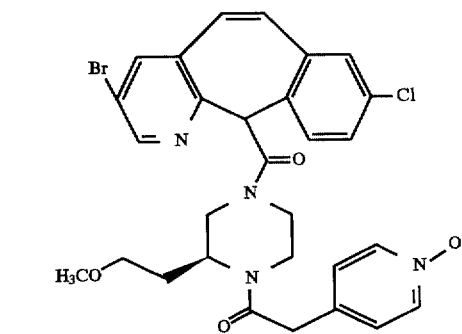

Step A:

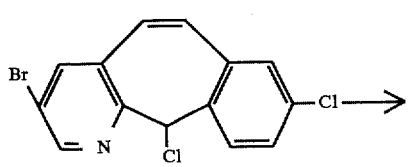

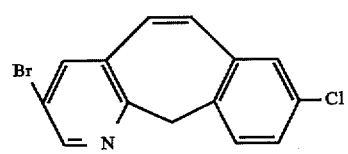

Follow the procedure of Example 1, Step A, using the product of Preparative Example 9 to obtain the product.

Step B:

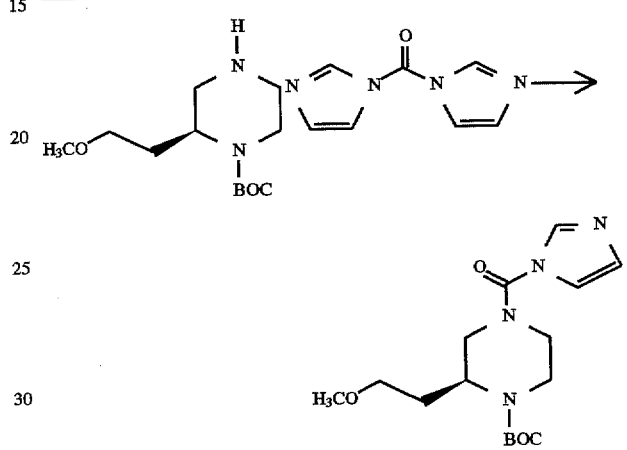

Follow the procedure of Example 1, Step B, to obtain the product.

Step C:

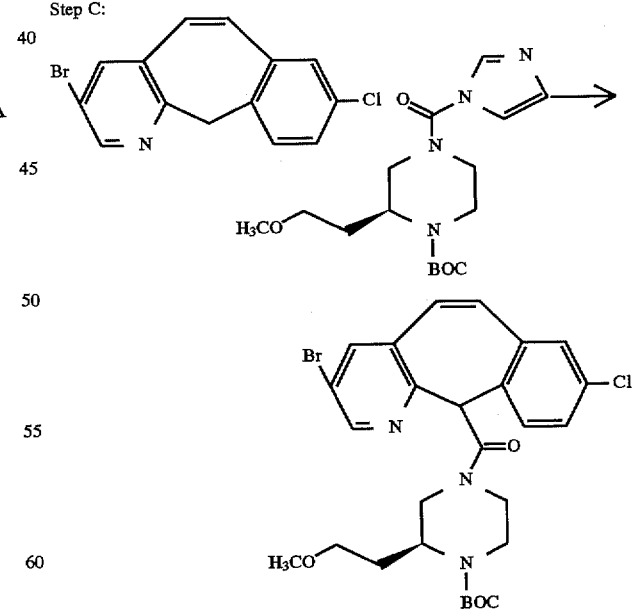

Follow the procedure of Example 1, Step C, using the products of Example 4, Steps A and B, to obtain the product.

Step D:

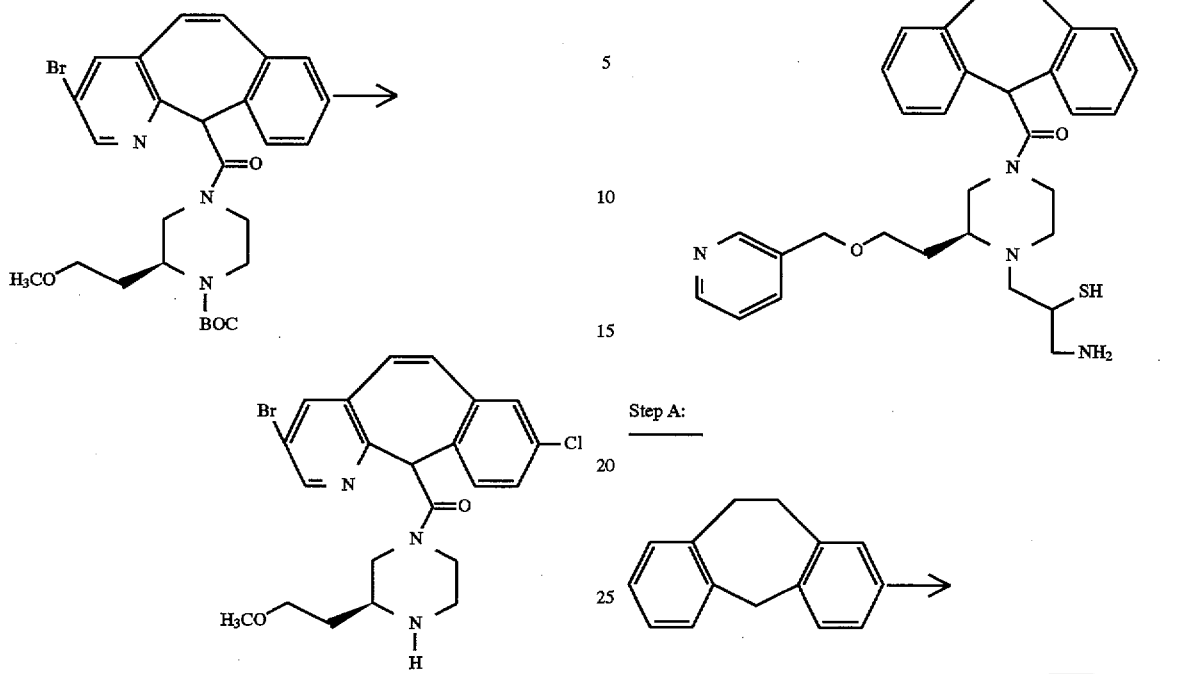

Follow the procedure of Example 1, Step D, using the product of Example 4, Step C, to obtain the product.

Step E:

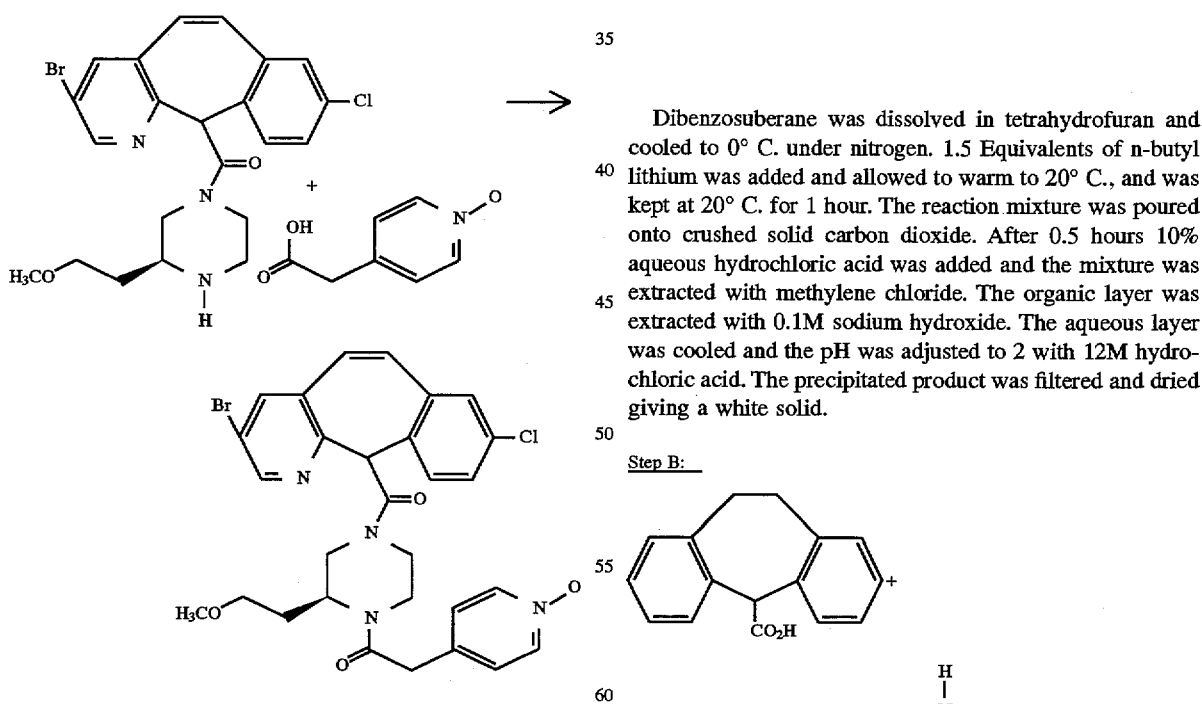

Follow the procedure of Example 2, Step A, using the product of Example 4, Step D, and Preparative Example 11, to obtain the product.

EXAMPLE 5

If one were to follow the procedures described in Steps A to F then one would obtain a compound of the formula:

Step A:

Step B:

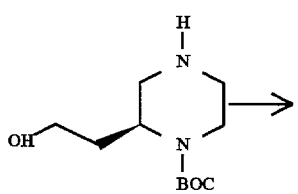

Dibenzosuberane was dissolved in tetrahydrofuran and cooled to 0° C. under nitrogen. 1.5 Equivalents of n-butyl lithium was added and allowed to warm to 20° C., and was kept at 20° C. for 1 hour. The reaction mixture was poured onto crushed solid carbon dioxide. After 0.5 hours 10% aqueous hydrochloric acid was added and the mixture was extracted with methylene chloride. The organic layer was extracted with 0.1M sodium hydroxide. The aqueous layer was cooled and the pH was adjusted to 2 with 12M hydrochloric acid. The precipitated product was filtered and dried giving a white solid.

51

-continued

Step B:

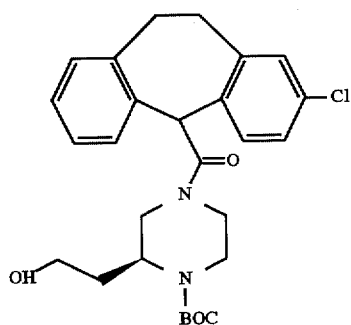

Make the piperazine reactant according to the procedure in Example 13 of WO95/00497. Follow the procedure of Example 2, Step A, above, to obtain the product.

Step C:

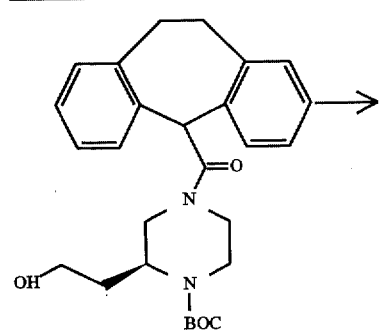

Dissolve the product of Step B in dry, degassed N,N-dimethylforamide and cool to 0° C. Add 1.3 equivalents of sodium hydride followed by 1.4 equivalents of 3-chloromethylpyridine. After 3 hours quench the reaction with saturated ammonium chloride solution. Concentrate under vacuo and partition between ethyl acetate and sodium bicarbonate solution. Dry the organic layer over magnesium sulfate, filter and concentrate under vacuo. Chromatograph the residue on silica gel using ethyl acetate-hexane.

52

Step D:

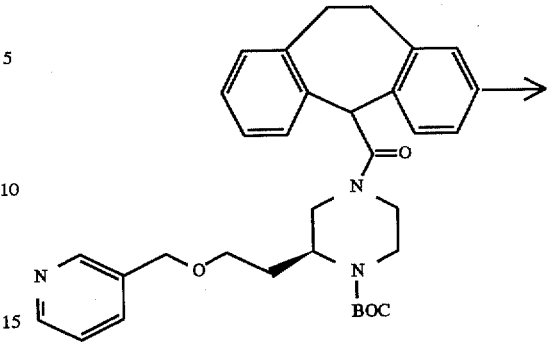

Follow the procedure of Example 1, Step D, to obtain the product.

Step E:

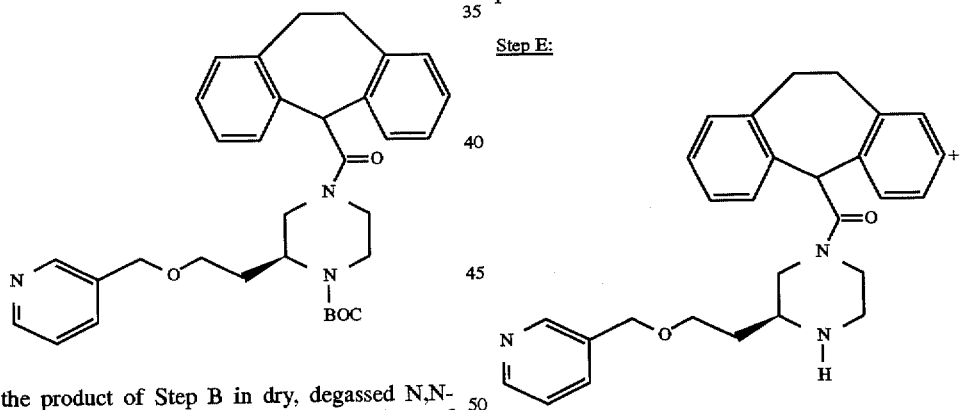

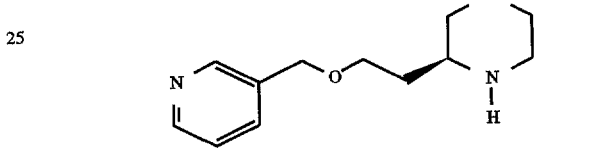

53
-continued

Step E:

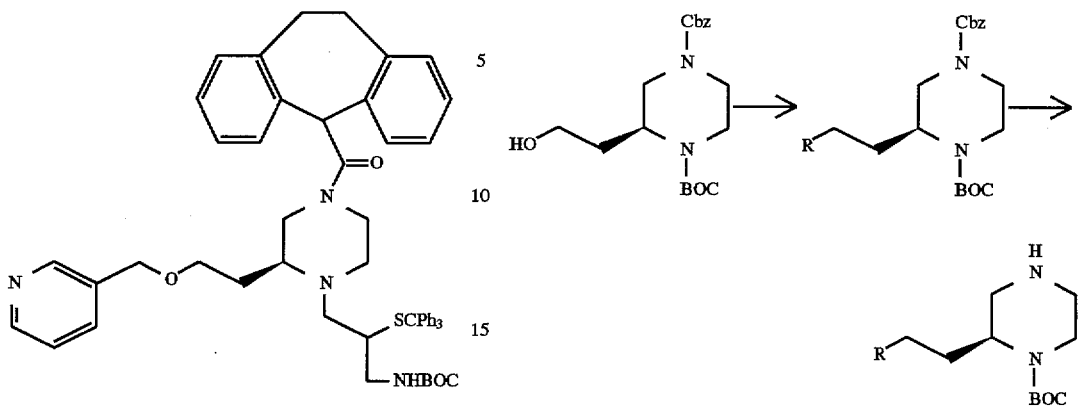

Prepare the reactant aldehyde by procedures similar to those described in Example 1 of WO95/00497. Follow the procedure of Example 1, Step E, above to obtain the product.

Step F:

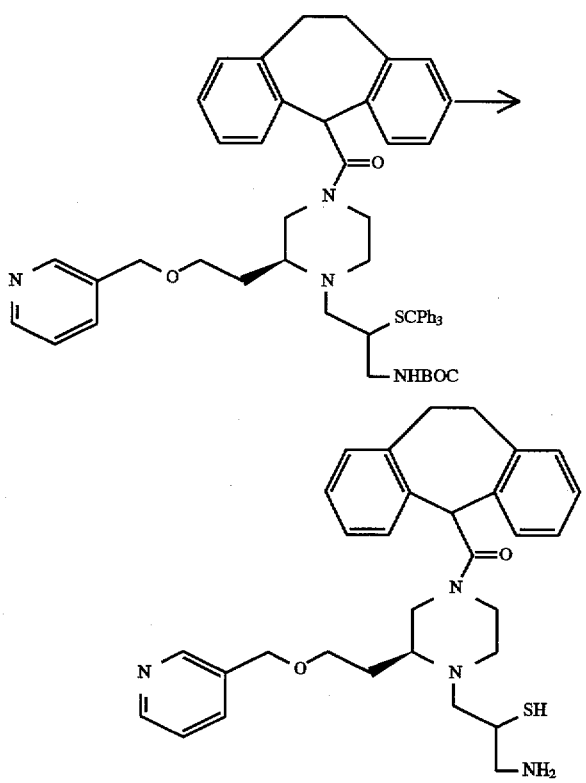

Follow the procedure of Example 1, Step F, to obtain the product.

EXAMPLES 6–10

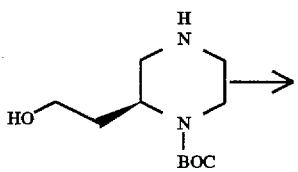

54
-continued

React the title compound of Example 13A of WO 95/00497 with benzyloxycarbonyl chloride according to standard conditions well known in the art, to obtain the N-Cbz (benzyloxycarbonyl) protected alcohol shown above. Purification of the protected alcohol, according to procedures well known in the art, and then reaction of the protected alcohol with the reagents in Column 1 of Table 2 would give the corresponding N-Cbz protected intermediates having R as defined in Column 2 of Table 2. After purification according to techniques well known in the art, the protected intermediate may be selectively deprotected (to remove the Cbz group) using mild catalytic hydrogenation procedures well known in the art. Following deprotection, purification by known techniques would yield the BOC-protected intermediate having the R group shown in Column 2 of Table 2.

TABLE 2

| Column 1 - (Reagents) | Column 2 - R Group |
|---|---|
| Example 6 | |
| 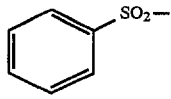 Cl and NaH | 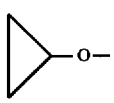 Prepare as described in Example 14 of WO 95/00497. |
| $C_6H_5SSC_6H_5$ + (n-Bu)$_3$P | Example 7 ⌬—SO$_2$— Prepare as described in Examples 20B and 20C of WO 95/00497. |
| (i) ⌬O⌬CH$_3$ + Hg(OAc)$_2$ + CH$_3$COOH (ii) CH$_2$I$_2$ + Et$_2$Zn | Example 8 △—O— Prepare as described in Examples 26A and 26B of WO 95/00497. |

TABLE 2-continued

| Column 1 - (Reagents) | Column 2 - R Group |
|---|---|
| (i) EtOCON=NCOOEt + (C₆H₅)₃P + CH₃COSH  (ii) NH₃ + CH₃OH + 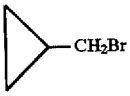—CH₂Br  (iii) Mg monoperphthalic acid + CH₃OH | Example 9  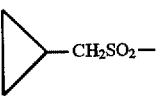—CH₂SO₂—  Prepare as described in Examples 29A, 29B and 29C of WO 95/00497. |
| n-C₃H₇I + NaH | Example 10  n-C₃H₇O—  Prepare as described in Example 13C of WO 95/00497. |

EXAMPLE 11

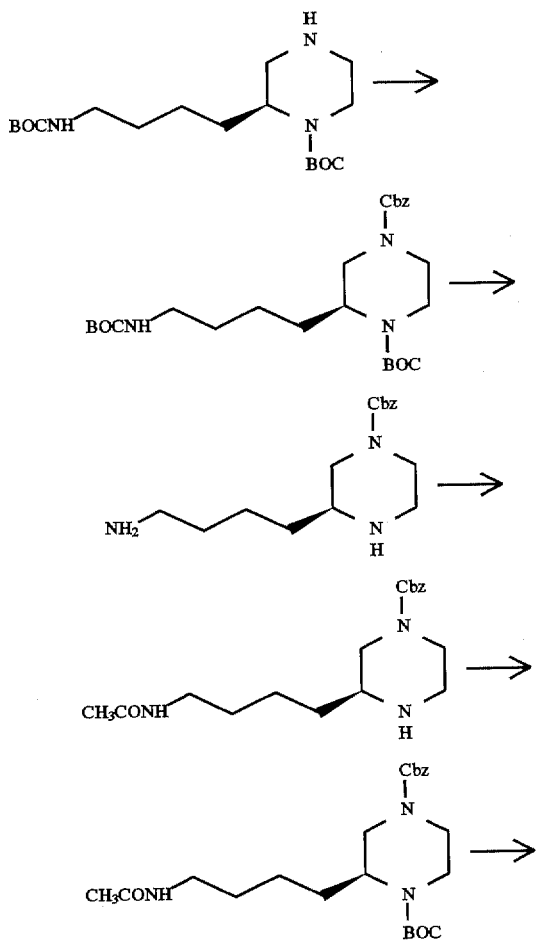

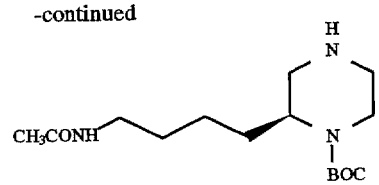

Convert the title compound from Example 27D of WO 95/00497, by the scheme shown above, using procedures well known in the art, into 1-tert-butoxycarbonyl-2(S)-(4-acetylaminobutyl)piperazine.

EXAMPLE 12

If one were to follow the procedures in Steps A to G, then one would obtain the compound:

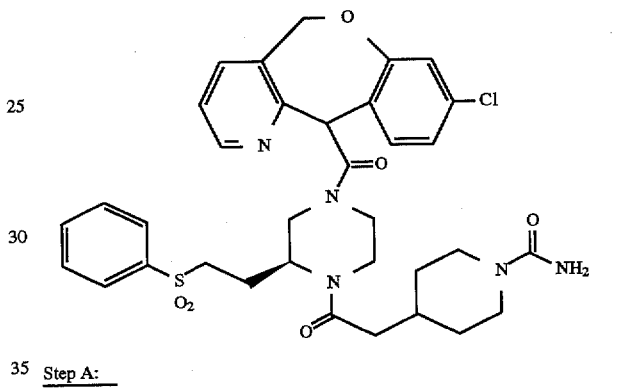

Step A:

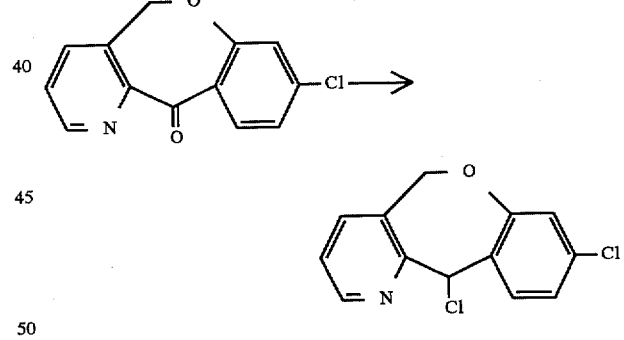

Prepare the starting material according to the procedure described in Example 4C of WO89/10369. Convert the starting material into the chloro product by the method described in U.S. Pat. No. 3,409,621.

Step B:

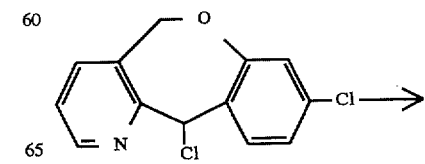

-continued
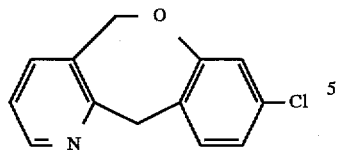
Follow the procedure in Example 1, Step A, to obtain the product.
Step C:
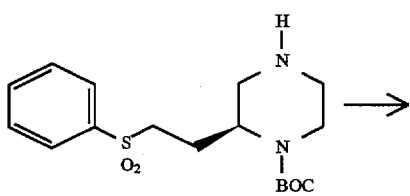
React the product of Step A with the product of Example 7 by the method of Example 1, Step B, to obtain the product.
Step D:
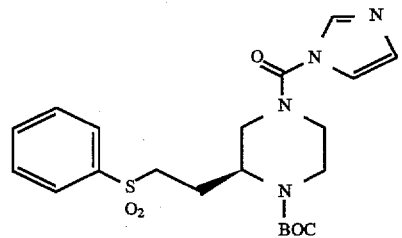
-continued
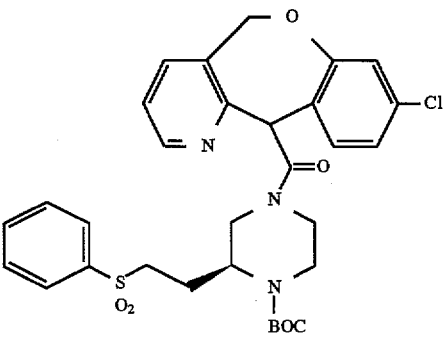
Follow the procedure in Example 1, Step C, to obtain the product.
Step E:
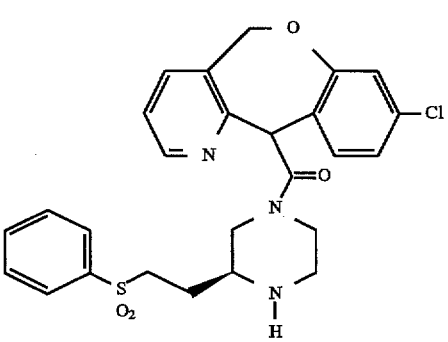
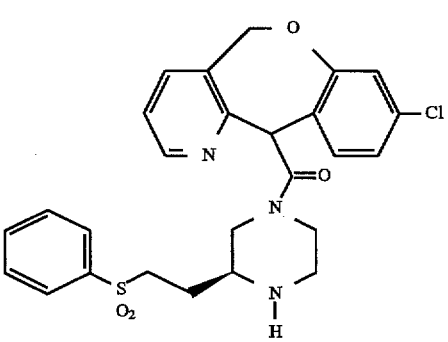
Follow the procedure in Example 1, Step D, to obtain the product.

Step F:

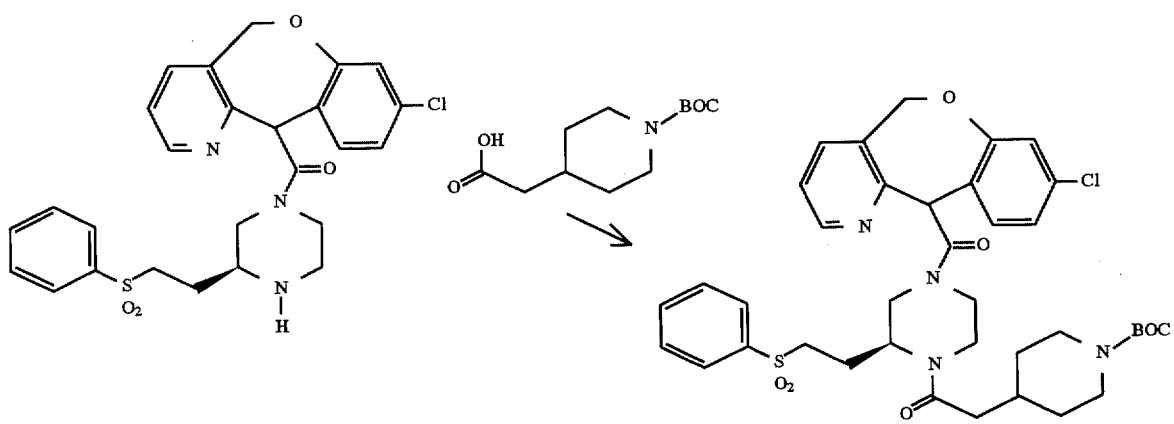

React the product of Example 12, Step E, with the BOC protected 4-piperidinylacetic acid of Preparative Example 5D, according to the procure in Example 2, Step A, to obtain the product.

Step G:

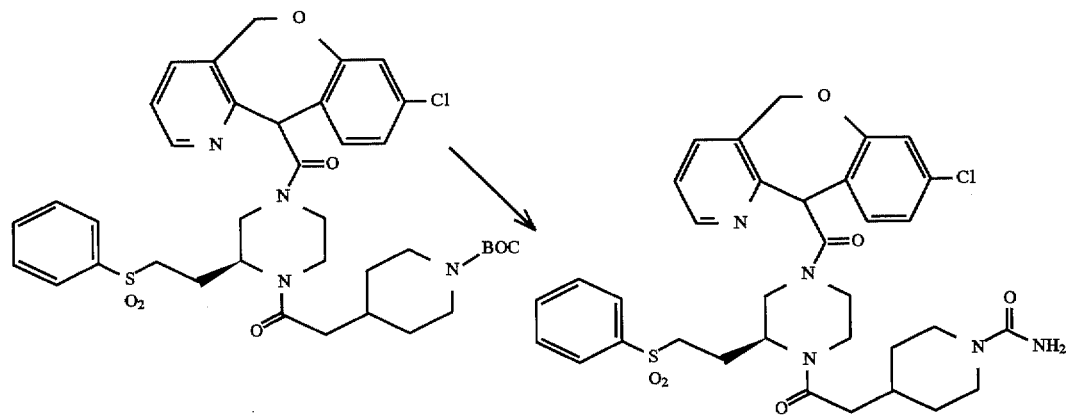

Dissolve the product of Step F in HCl-Dioxane and stir for 1 hour. Concentrate in vacuo. Partition between sodium bicarbonate solution and ethyl acetate. Dry the organic layer over magnesium sulfate, filter and concentrate under vacuo. Dissolve the residue in methylene chloride and add excess trimethylsilylisocyanate. Stir under nitrogen for 18 hours. Add additional trimethylsilylisocyanate and stir until the reaction is complete. Wash with aqueous sodium bicarbonate solution. Dry the organic layer over magnesium sulfate, filter and concentrate in vacuo. Chromatograph the residue on silica gel using methanol-methylene chloride to give the product.

EXAMPLE 13

If one were to follow the procedures in Steps A to E, then one would obtain the compound:

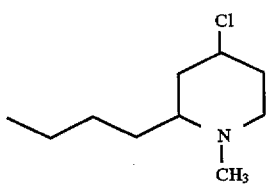

Step A:

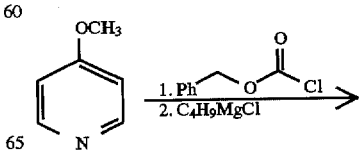

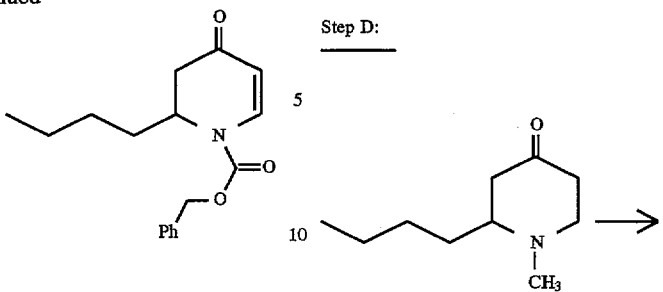

According to the procedure of D. L. Comins, et al., in Tat. Lett., 4549 (1986), dissolve 4-methoxypyridine in THF and cool to −23° C. Add benzylchloroformate dropwise (1 equivalent) followed by 1 equivalent of butyl magnesium chloride in THF added dropwise. Pour into 10% hydrochloric acid and extract with ether. Dry over MgSO$_4$ and concentrate. (Ph in the above formula represents phenyl).

Step B:

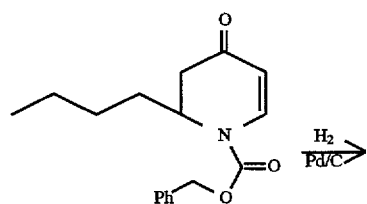

Dissolve the product of Step A in ethanol containing 10% palladium on carbon and hydrogenate at 60 psi. Filter and concentrate under vacuo to obtain the product.

Step C:

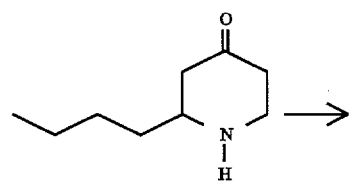

Dissolve the product of Step B in tetrahydrofuran, cool to 0° C. under nitrogen and add one equivalent of sodium hydride. After stirring for 15 minutes, one equivalent of methyl iodide is added. Stir the reaction for 15 minutes, concentrate under vacuo and chromatograph on silica gel using methanol-methylene chloride.

Step D:

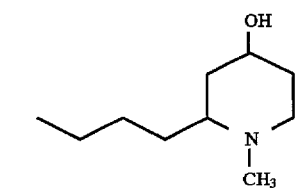

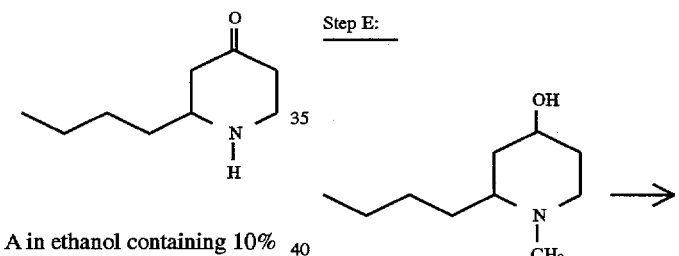

Dissolve the product of Step C in ethanol and add an excess of sodium borohydride. Concentrate under vacuo. Partition between water and ethyl acetate. Dry the organic layer over magnesium sulfate, filter and concentrate under vacuo.

Step E:

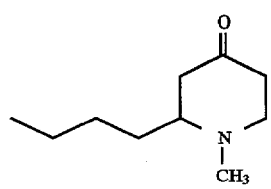

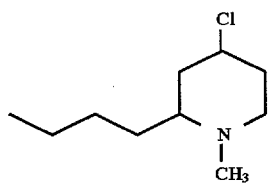

Dissolve the product of Step D in pyridine containing an excess of thionyl chloride. Stir for 18 hours and concentrate in vacuo. Partition between ethyl acetate and aqueous sodium bicarbonate. Dry the organic layer over magnesium sulfate, filter and concentrate in vacuo to obtain the product.

EXAMPLE 14

If one were to follow the procedure of Steps A to F, then one would obtain the compound:

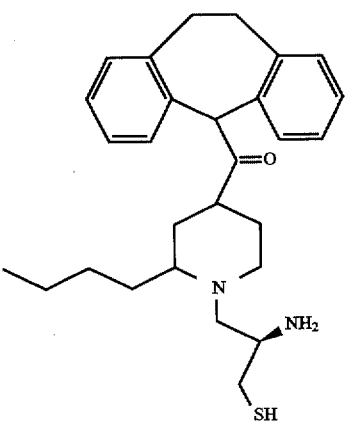

Step A:

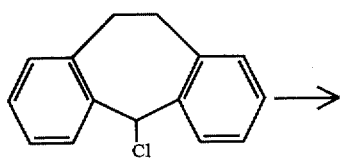

5-chlorodibenzosuberane, 48.18 g (0.2 mole), was dissolved in 400 mL of toluene. Silver cyanide, 36.7 g (0.27 mole), was added and the mixture was refluxed for 24 hours. The mixture was cooled, filtered and concentrated in vacuo. The residue was recrystallized from 2-propyl ether and hexane to give 38.8 g of the product. MP=94.2°–94.9° C.

Step B:

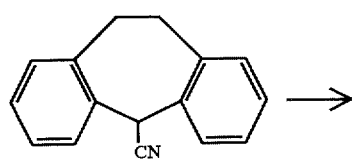

Dissolve the product of Example 12, Step E, in THF and add one equivalent of magnesium. Stir until all of the magnesium has reacted. Add this solution dropwise to a solution of one equivalent of the product of Step A in THF. Stir for 1 hour then quench with aqueous ammonium chloride solution. Extract with ethyl acetate. Dry the organic layer over magnesium sulfate, filter and concentrate under vacuo. Chromatograph on silica gel using methanol-methylene chloride to obtain the product.

Step C:

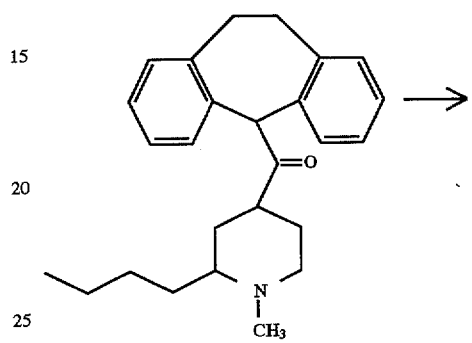

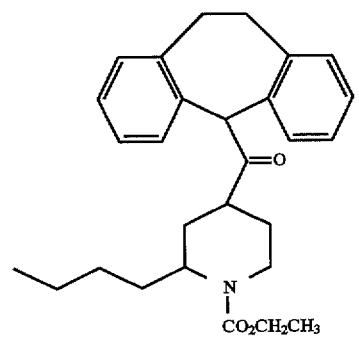

Dissolve the product of Step B in dry toluene containing 2 equivalents of triethylamine. Warm to 80° C. and add 9 equivalents of ethyl chloroformate. Stir at 80° C. until the reaction is complete, about 2 hours. Filter and concentrate under vacuo. Chromatograph on silica gel using ethyl acetate-hexane to obtain the product.

Step D:

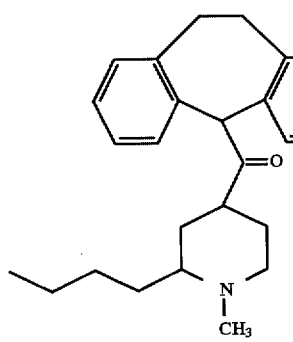

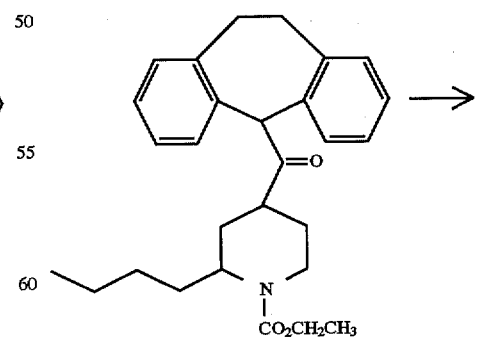

Step F:

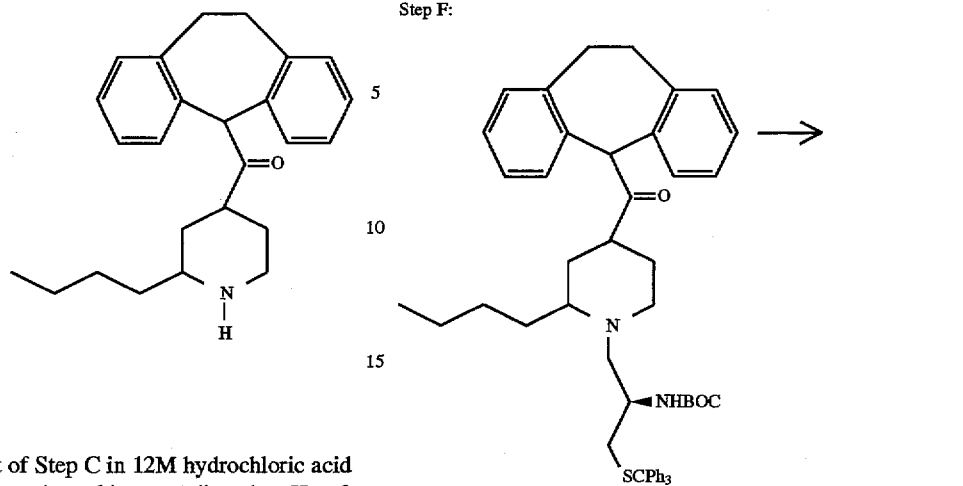

Dissolve the product of Step C in 12M hydrochloric acid and reflux until complete, about 6 hours. Adjust the pH to 8 with solid sodium hydroxide and filter the precipitated product. Chromatograph on silica gel using methanol-methylene chloride and ammonium hydroxide to give the product.

Step E:

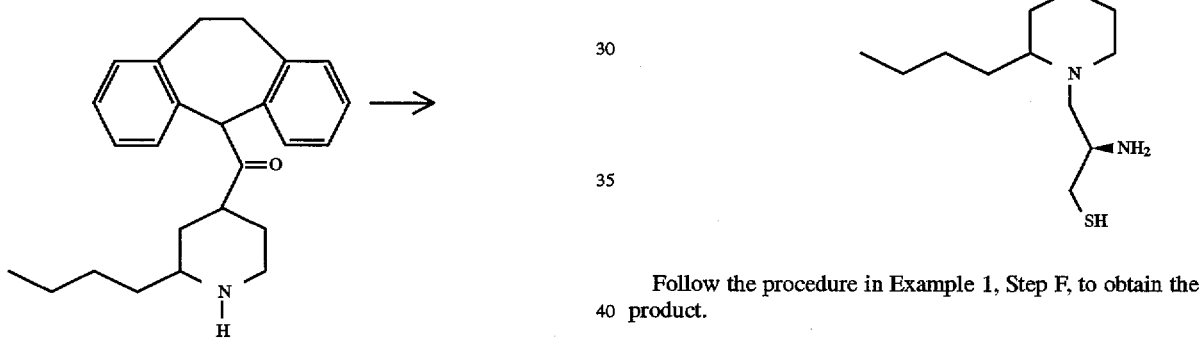

Follow the procedure in Example 1, Step F, to obtain the product.

EXAMPLE 15

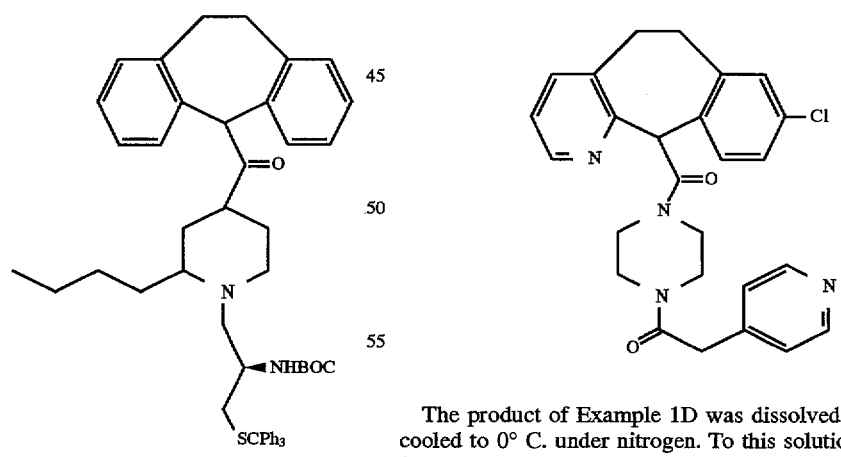

The product of Example 1D was dissolved in DMF and cooled to 0° C. under nitrogen. To this solution was added 2 equivalents of 4-pyridyl acetic acid, 6 equivalents of triethylamine, 2 equivalents of 1-hydroxybenzotriazole (HOBT), and 2 equivalents of DEC. The reaction mixture was stirred at 0° C. overnight. Then the reaction mixture was diluted with aqueous sodium bicarbonate solution and extracted with ethyl acetate. The organic layer was concen- Follow the procedure in Example 1, Step E, to obtain the product.

trated under vacuo and the residue was chromatographed on silica gel using methanol-methylene chloride as the solvent. Fractions containing the product were concentrated under vacuo to give the title compound as a white foam. M+1=461.

EXAMPLE 16

If one were to follow the procedure described below, then one would obtain the indicated compound:

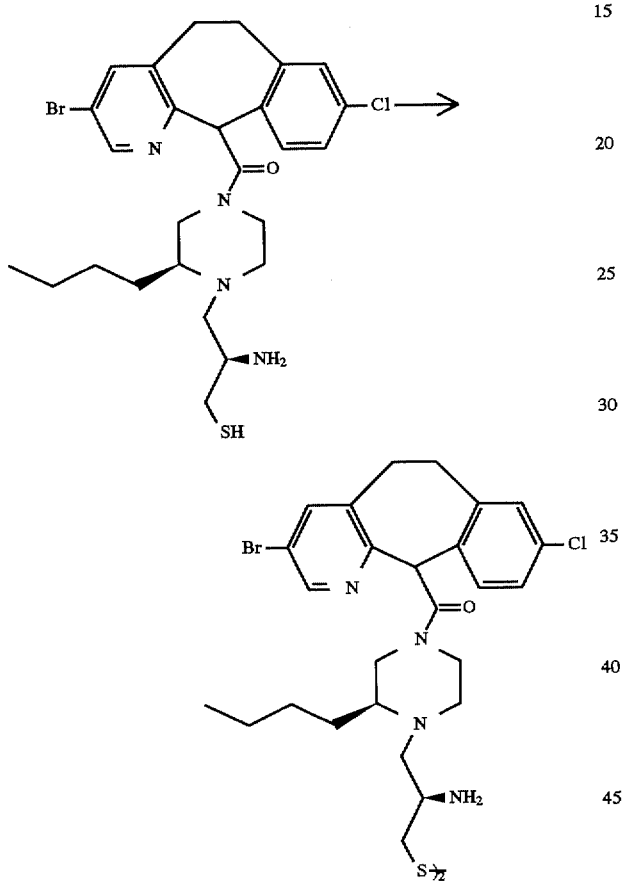

Add a solution of iodine in methanol to the product of Example 3, Step F, in methanol until a slight yellow color persists. Concentrate in vacuo and chromatograph the residue by HPLC using a $C_{18}$ column and a solvent of wateracetonitrile and 0.1% trifluoroacetic acid. Concentrate in vacuo to give the product.

EXAMPLE 17

If one were to follow the procedure described, then one would obtain the compound:

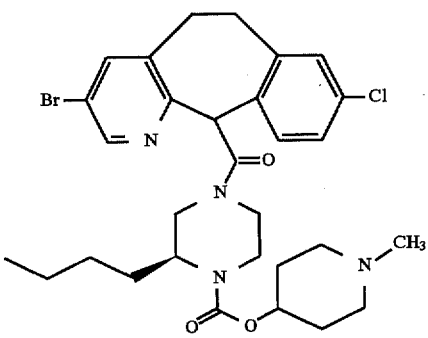

React the product of Example 3D with the product of Preparative Example 17 in dichloromethane in the presence of pyridine at 25° C. for 20 to 100 hours to give the title compound.

EXAMPLE 18

If one were to follow the procedure described, then one would obtain the compound:

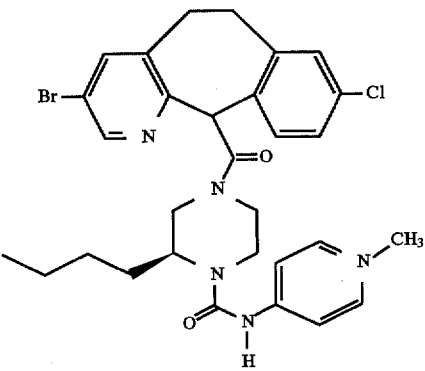

Heat he product (acylazine) from Preparative Example 13 under reflux in anhydrous toluene to convert it into the corresponding isocyanate in situ. Add the product of Example 3D in anhydrous toluene to the mixture and stir this mixture at 25° C. for 20 hours to give the title compound.

ASSAYS

The utility of the compounds of the present invention can be demonstrated by the following assay procedures.

1. In vitro enzyme assays: Inhibition of farnesyl protein transferase and geranylgeranyl protein transferase.

Both farnesyl protein transferase (FPT) and geranylgeranyl protein transferase (GGPT) I are partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyltransferase from bovine brain: Implications for protein prenylation specificity, Proc. Natl. Aced. Sci USA 88:5302–5306, the disclosure of which is incorporated herein by reference thereto). Human farnesyl protein transferase is also expressed in E. coli, using cDNA clones encoding both the α and β subunits. The methods used are similar to those published (Omer, C. et al., (1993). Characterization of recombinant human farnesyl protein transferase: Cloning, expression, farnesyl diphosphate binding, and functional homology with yeast prenyl-protein transferases, Biochemistry 32:5167–5176). Human farnesyl protein transferase is partially-purified from the soluble protein fraction of *E. coli* as described above. The tricyclic farnesyl protein transferase inhibitors disclosed herein inhibit both human and rat enzyme with similar potencies. Two forms of val$^{12}$-Ha-Ras protein are prepared as substrates for these enzymes, differing in their carboxy terminal sequence. One form terminates in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins are constructed so that the proteins contain an amino-terminal extension of 6 histidine residues. Both proteins are expressed in *Escherichia coli* and purified using metal chelate affinity chromatography. The radiolabelled isoprenyl pyrophosphate substrates, [$^3$H]farnesyl pyrophosphate and [$^3$H]geranylgeranyl pyrophosphate, are purchased from a commercial source, such as DuPont/New England Nuclear.

Several methods for measuring farnesyl protein transferase activity are known (Reiss et al 1990, Cell 62:81; Schaber et al 1990, J. Biol. Chem. 265:14701; Manne et al 1990, PNAS 8.7:7541; and Barbacid & Manne 1993, U.S. Pat. No. 5,185,248). The activity is assayed by measuring the transfer of [$^3$H]farnesyl from [$^3$H]farnesyl pyrophosphate to Ras-CVLS using conditions similar to those described by Reiss et al., 1990 (Cell 62:81) The reaction mixture contains 40 mM Hepes, pH 7.5; 20 mM magnesium chloride; 5 mM dithiothreitol; 0.25 µM [$^3$H]farnesyl pyrophosphate; 10 µl Q-Sepharose-purified farnesyl protein transferase; the indicated concentration of tricyclic compound or dimethylsulfoxide (DMSO) vehicle control (5% DMSO final); and 5 µM Ras-CVLS in a total volume of 100 µl. The reaction is allowed to proceed for 30 minutes at room temperature and then stopped with 0.5 ml of 4% sodium dodecyl sulfate (SDS) followed by 0.5 ml of cold 30% trichloracetic acid (TCA). Samples are allowed to sit on ice for 45 minutes and precipitated Ras protein is then collected on GF/C filter paper mats using a Brandel cell harvester. Filter mats are washed once with 6% TCA, 2% SDS and radioactivity is measured in a Wallac 1204 Betaplate BS liquid scintillation counter. Percent inhibition is calculated relative to the DMSO vehicle control.

The geranylgeranyl protein transferase I assay is essentially identical to the farnesyl protein transferase assay described above, with two exceptions: [$^3$H] geranylgeranylpyrophosphate replaces farnesyl pyrophosphate as the isoprenoid donor and Ras-CVLL is the protein acceptor. This is similar to the assay reported by Casey et al (Casey, P. J., et al., (1991), Enzymatic modification of proteins with a geranylgeranyl isoprenoid, Proc. Natl. Aced. Sci, USA 88:8631–8635, the disclosure of which is incorporated herein by reference).

2. Cell-Based Assay: Transient expression of val$^{12}$-Ha-Ras-CVLS and val$^{12}$-Ha-Ras-CVLL in COS monkey kidney calls: Effect of farnesyl protein transferase inhibitors on Ras processing end on disordered cell growth induced by transforming Ras.

COS monkey kidney cells are transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells are plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media is removed and fresh media containing the appropriate drugs is re-added.

48 hours after electroporation cells are examined under the microscope to monitor disordered cell growth induced by transforming Ras. Cells expressing transforming Ras become more rounded and refractile and overgrow the monolayer, reminiscent of the transformed phenotype. Cells are then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 µM leupeptin; and 0.1 µM pepstatin. Cells are lysed by homogenization and cell debris is removed by centrifugation at 2000×g for 10 min.

Cellular protein is precipitated by addition of ice-cold trichloroacetic acid and redissolved in 100 µl of SDS-electrophoresis sample buffer. Samples (5–10 µl) are loaded onto 14% polyacrylamide minigels (Novex, Inc.) and electrophoresed until the tracking dye neared the bottom of the gel. Proteins resolved on the gels are electroblotted onto nitrocellulose membranes for immunodetection.

Membranes are blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family, J. Virol. 43:294–304), in PBS containing 1% fetal calf serum for one hour at room temperature. After washing, membranes are incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL is detected using a colorimetric peroxidase reagent (4-chloro-1-naphthol) as described by the manufacturer (Bio-Rad).

3. Cell Mat Assay;

Normal human HEPM fibroblasts are planted in 3.5 cm dishes at a density of 5×10$^4$ cells/dish in 2 ml growth medium, and incubated for 3–5d to achieve confluence. Medium is aspirated from each dish and the indicator tumor cells, T24-BAG4 human bladder carcinoma cells expressing an activated H-ras gene, are planted on top of the fibroblast monolayer at a density of 2×10$^3$cells/dish in 2 ml growth medium, and allowed to attach overnight. Compound-induced colony inhibition is assayed by addition of serial dilutions of compound directly to the growth medium 24 h after tumor cell planting, and incubating cells for an additional 14 d to allow colony formation. Assays are terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci. 84, 156–160(1987)). In the colony inhibition assay, compounds are evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values are obtained by determining the density of tumor cells and mat cells by visual inspection and enumeration of cells per colony and the number of colonies under the microscope. The therapeutic index of the compound is quantitatively expressed as the ratio of mIC$_{50}$/tIC$_{50}$, with values greater than one indicative of tumor target specificity.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method Of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations am intended to fall within the spirit and scope of the present invention.

What is claimed is:
1. A compound of the formula:
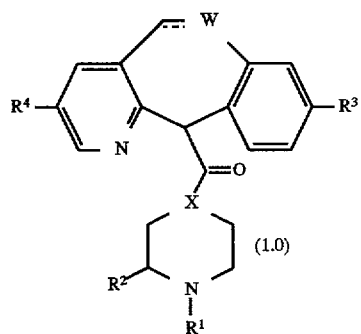
(1.0)
or a pharmaceutically acceptable salt or solvate thereof, wherein:
(1) $R^1$ is a group selected from:
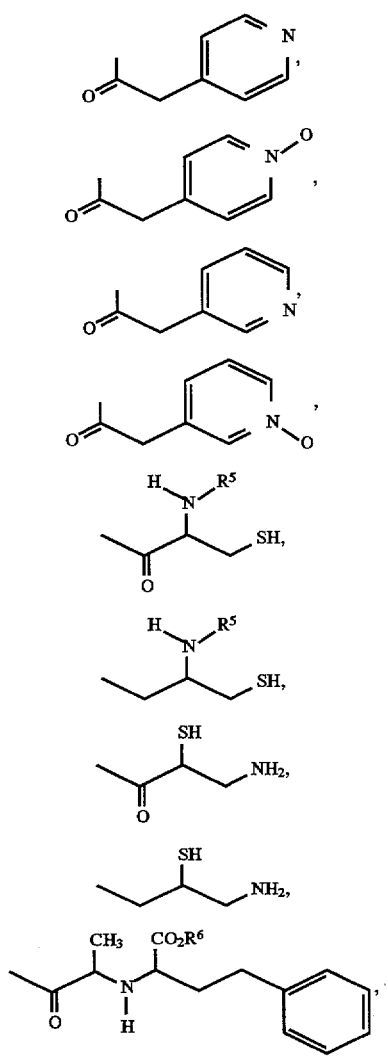
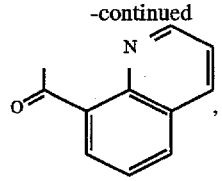
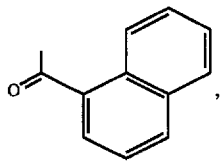
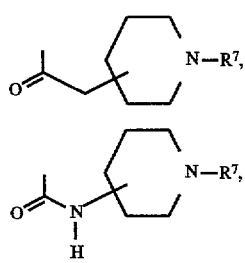
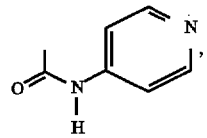
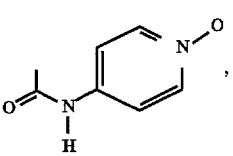
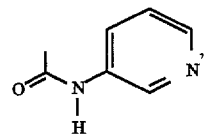
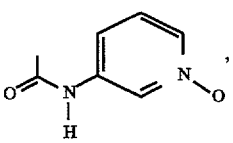
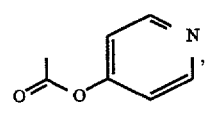
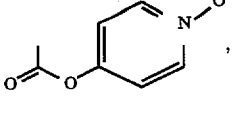
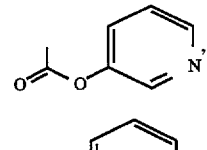
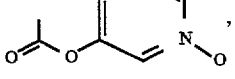

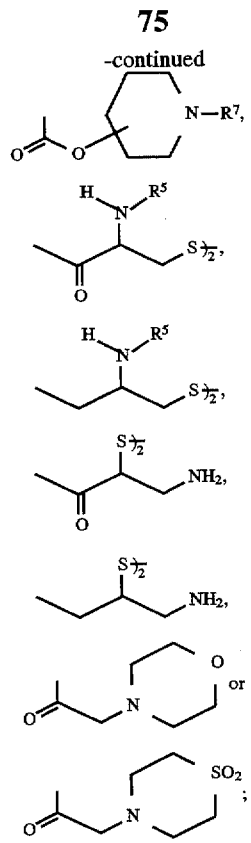

R² is selected from:
(1) H,
(2) $C_1$ to $C_8$ alkyl,
(3) $C_2$ to $C_8$ alkenyl,
(4) $C_2$ to $C_8$ alkynyl,
(5)

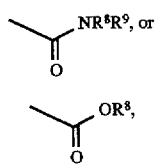

wherein said alkyl, alkenyl, or alkynyl is optionally substituted with one or more groups independently selected from:

(a) aryl, aralkyl, heteroaryl, heteroarylalkyl or heterocycloalkyl; said aryl, aralkyl, heteroaryl, heteroarylalkyl or heterocycloalkyl optionally substituted with one or more groups independently selected from:

(1) $C_1$ to $C_4$ alkyl,
(2) $(CH_2)_tOR^8$ wherein t is 1 to 4,
(3) $(CH_2)_tNR^8R^9$ wherein t is 1 to 4, or
(4) halogen,
(b) $C_3$ to $C_6$ cycloalkyl,
(c) —$OR^8$,
(d) —$SR^8$,
(e) —$S(O)R^8$,
(f) —$SO^2R^8$,
(g) —$NR^8R^9$,

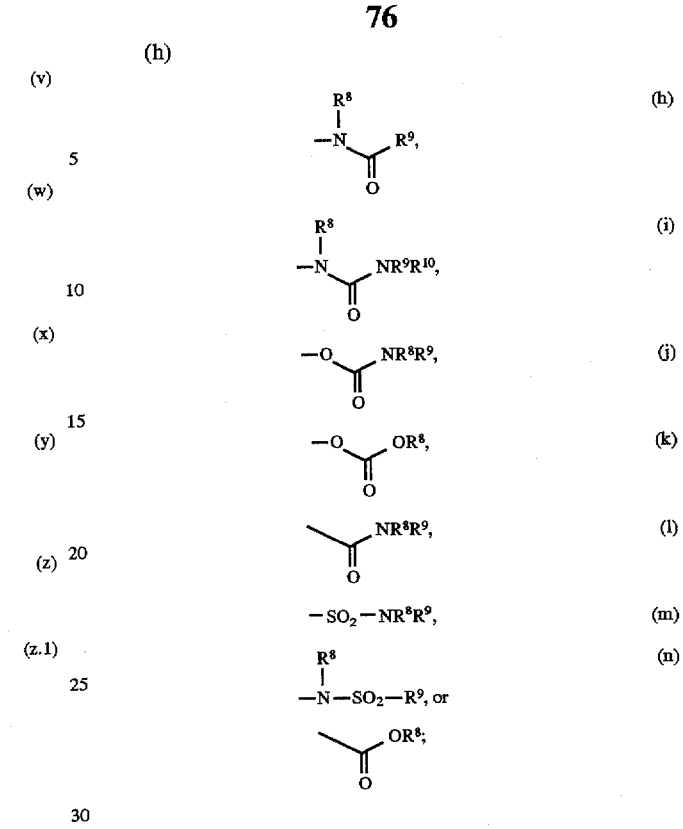

R³ is selected from H, halogen or $C_1$ to $C_6$ alkyl;
R⁴ is selected from H, halogen or $C_1$ to $C_6$ alkyl;
R⁵ is selected from: H, R⁶ is selected from H or $C_1$ to $C_6$ alkyl;
R⁷ is selected from H, $C_1$ to $C_6$ alkyl, haloalkyl, or —C(O)R¹¹ wherein R¹¹ is selected from $C_1$ to $C_6$ alkyl, $C_1$ to $C_6$ alkoxy or —NHR¹² (wherein R¹² is $C_1$ to $C_6$ alkyl or H), or R⁷ is an acyl radical of a naturally occurring amino acid;

R⁸, R⁹ and R¹⁰ are independently selected from H, $C_1$ to $C_4$ alkyl, $C_3$ to $C_6$ cycloalkyl, heteroaryl, heteroarylalkyl, heterocycloalkyl, aryl or aralkyl; said alkyl, cycloalkyl, heteroaryl, heteroarylalkyl, heterocycloalkyl, aryl or aralkyl are optionally substituted with $C_1$ to $C_4$ alkoxy, aryl, heteroaryl, heterocycloalkyl, cyclopropyl, halogen, —OH, —C(O)R¹³, —$SO_2R^{13}$, or —NR¹⁴R¹⁵ wherein R¹³ is selected from $C_1$ to $C_4$ alkyl or aralkyl, and wherein R¹⁴ and R¹⁵ are independently selected from H, $C_1$ to $C_4$ alkyl or aralkyl; with the proviso that R⁸ is not H in substituents (e), (f) or (k), and with the proviso that $R^9$ is not H in substituent (h) or (n), and with the proviso that $R^8$, $R^9$, or $R^{10}$ is not —$CH_2OH$ or —$CH_2NR^{14}R^{15}$ when $R^8$, $R^9$, or $R^{10}$ is directly attached to a heteroatom;

optionally, when $R^8$ and $R^9$ are bound to the same nitrogen, $R^8$ and $R^9$, together with the nitrogen to which they are bound, form a 5 to 7 membered heterocycloalkyl ring;

optionally, when $R^9$ and $R^{10}$ are bound to the same nitrogen, $R^9$ and $R^{10}$, together with the nitrogen to which they are bound, form a 5 to 7 membered heterocycloalkyl ring;

—represents an optional bond;

W is selected from CH when the optional bond is present, or O, S or $CH_2$ when the optional bond is absent;

X is N; and

Y is selected from N or CH.

2. The compound of claim 1 wherein $R^3$ and $R^4$ are halogen.

3. The compound of claim 2 wherein $R^3$ is Cl and $R^4$ is Br.

4. The compound of claim 1 wherein Y is N.

5. The compound of claim 1 wherein $R^1$ is selected from

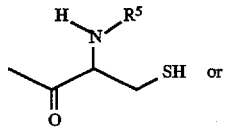
(e)

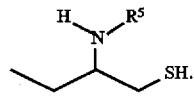
(f)

6. The compound of claim 5 wherein $R^5$ is H.

7. The compound of claim 1 wherein $R^2$ is selected from H, —$C_4H_9$, —$CH_2C_6H_5$, —$CH_2CH_2OCH_3$, —$CH_2CH_2SCH_3$, —$CH_2CH_2O$-n-$C_3H_7$, —$CH_2CH_2CH_2OCH_3$,

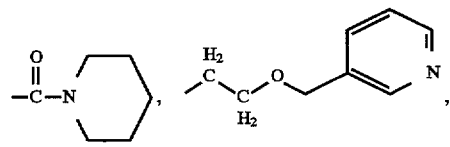

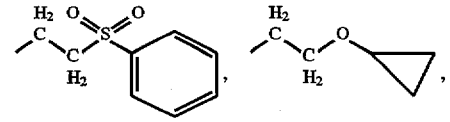

8. The compound of claim 1 wherein W is CH or $CH_2$, and Y is N.

9. The compound of claim 8 wherein $R^3$ is Cl and $R^4$ is Br.

10. The compound of claim 9 wherein $R^1$ is selected from

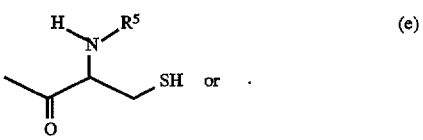
(e)

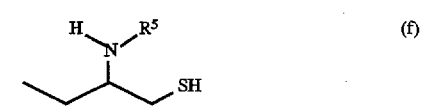
(f)

wherein $R^5$ is H, and $R^2$ is selected from H, —$C_4H_9$, —$CH_2C_6H_5$, —$CH_2CH_2OCH_3$, —$CH_2CH_2SCH_3$, —$CH_2CH_2O$-n-$C_3H_7$, —$CH_2CH_2CH_2OCH_3$,

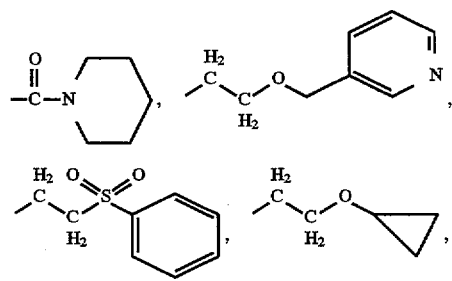

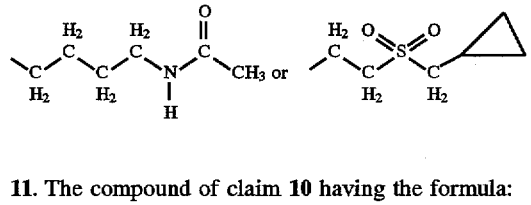

11. The compound of claim 10 having the formula:

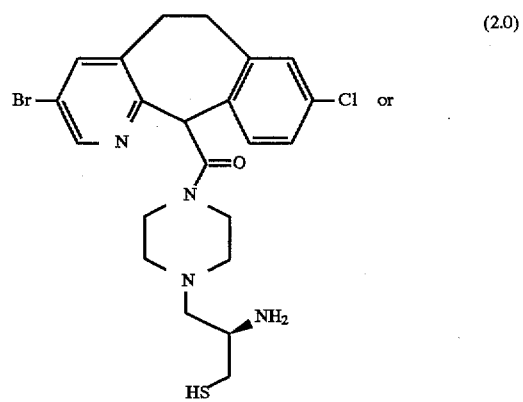
(2.0)

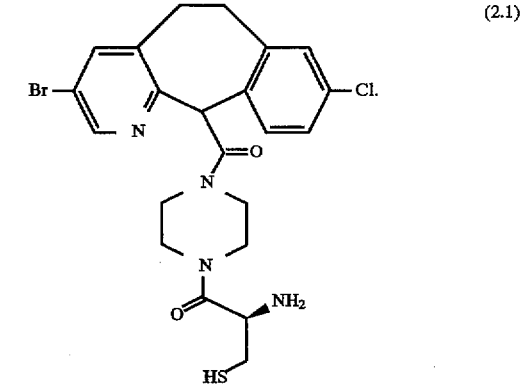
(2.1)

12. A method for inhibiting the abnormal growth of cells comprising administering an effective amount of a compound of claim 1.

13. The method of claim 12 wherein the the cells inhibited are tumor cells expressing an activated ras oncogene.

14. The method of claim 12 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

15. The method of claim 12 wherein the inhibition of the abnormal growth of cells occurs by the inhibition of farnesyl protein transferase.

16. The method of claim 12 wherein the inhibition is of tumor cells wherein the Ras protein is activated as a result of oncogenic mutation in genes other than the Ras gene.

17. A pharmaceutical composition for inhibiting the abnormal growth of cells comprising an effective amount of compound of claim 1 in combination with a pharmaceutically acceptable carrier.

18. The compound of claim 1 wherein $R^1$ is selected from:

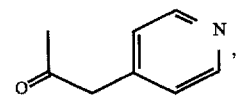 (a)

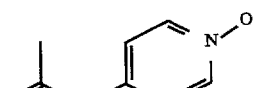 (b)

 (c)

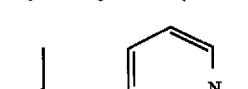 (d)

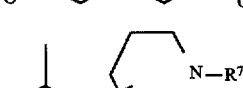 (l)

 (z.1)

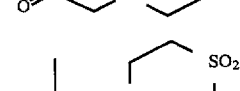 (z.2)

19. The compound of claim 1 wherein $R^1$ is selected from:

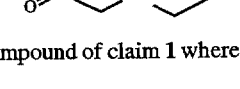 (m)

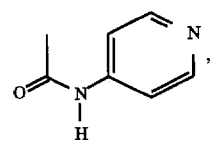 (n)

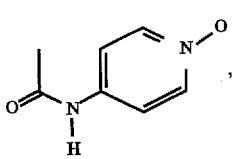 (o)

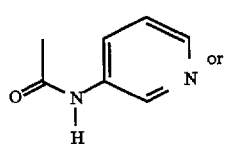 (p)

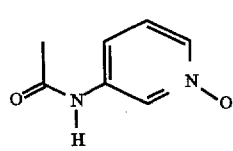 (q)

20. The compound of claim 1 wherein $R^1$ is selected from:

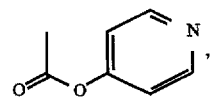 (r)

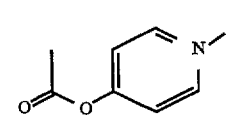 (s)

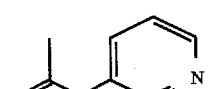 (t)

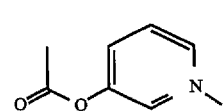 (u)

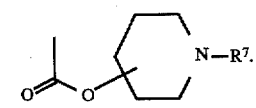 (v)

* * * * *